(12) United States Patent
Jones et al.

(10) Patent No.: US 7,709,483 B2
(45) Date of Patent: May 4, 2010

(54) PYRROLO-QUINOXALINONE DERIVATIVES AS ANTIBACTERIALS

(75) Inventors: Graham Elgin Jones, Harlow (GB); Timothy James Miles, Harlow (GB); Neil David Pearson, Harlow (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 12/295,749

(22) PCT Filed: Mar. 29, 2007

(86) PCT No.: PCT/EP2007/053056

§ 371 (c)(1),
(2), (4) Date: Oct. 2, 2008

(87) PCT Pub. No.: WO2007/115947

PCT Pub. Date: Oct. 18, 2007

(65) Prior Publication Data

US 2009/0062265 A1    Mar. 5, 2009

(30) Foreign Application Priority Data

Apr. 6, 2006  (GB) ................... 0606970.2
Mar. 26, 2007 (GB) ................... 0706023.9

(51) Int. Cl.
*A61K 31/495* (2006.01)

(52) U.S. Cl. .................. 514/250; 544/235; 544/354; 546/115; 546/199

(58) Field of Classification Search ............ 514/250; 544/235, 354; 546/115, 199
See application file for complete search history.

(56) References Cited

U.S. PATENT DOCUMENTS 4,603,199 A    7/1986 Gerster et al. .............. 544/105

FOREIGN PATENT DOCUMENTS

| WO | WO2006002047  | 6/2004  |
|----|---------------|---------|
| WO | WO2007081597  | 10/2005 |
| WO | WO2007071936  | 12/2005 |
| WO | WO 2006/014580 | 2/2006 |
| WO | WO2007122258  | 4/2006  |
| WO | WO2008003690  | 7/2006  |
| WO | WO2008116815  | 3/2007  |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, 18.*
Hackam, et al. JAMA, 296(14), 2006, 1731-1732.*

* cited by examiner

*Primary Examiner*—James O Wilson
*Assistant Examiner*—Douglas M Willis
(74) *Attorney, Agent, or Firm*—Reid S. Willis; John Lemanowicz

(57) ABSTRACT

Tricyclic nitrogen containing compounds and their use as antibacterials.

8 Claims, No Drawings

PYRROLO-QUINOXALINONE DERIVATIVES AS ANTIBACTERIALS

This application is a 371 of International Application No. PCT/EP2007/053056, filed 29 Mar. 2007, and claims the priority of GB 0606970.2, filed 6 Apr. 2006, and GB 0706023.9, filed 26 Mar. 2007, all of which are incorporated herein in their entirety.

BACKGROUND OF THE INVENTION

This invention relates to novel compounds, compositions containing them and their use as antibacterials.

WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO2006002047, WO2006014580, WO2006010040, WO2006017326, WO2006012396, WO2006017468, WO2006020561, WO2006081179, WO2006081264, WO2006081289, WO2006081178, WO2006081182, WO01/25227, WO02/40474, WO02/07572, WO2004024712, WO2004024713, WO2004035569, WO2004087647, WO2004089947, WO2005016916, WO2005097781, WO2006010831, WO2006021448, WO2006032466, WO2006038172, WO2006046552, WO06099884, WO06126171, WO06137485, WO06105289, WO06125974 and WO06134378 disclose quinoline, naphthyridine, morpholine, cyclohexane, piperidine and piperazine derivatives having antibacterial activity. WO2004104000 discloses tricyclic condensed ring compounds capable of selectively acting on cannabinoid receptors.

SUMMARY OF THE INVENTION

This invention provides a compound of formula (I) or a pharmaceutically acceptable salt, solvate and/or N-oxide thereof:

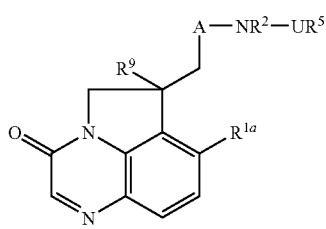

wherein:

$R^{1a}$ is selected from hydrogen; halogen; cyano; $(C_{1-6})$alkyl; $(C_{1-6})$alkylthio; trifluoromethyl; trifluoromethoxy; carboxy; hydroxy optionally substituted with $(C_{1-6})$alkyl or $(C_{1-6})$alkoxy-substituted$(C_{1-6})$alkyl; $(C_{1-6})$alkoxy-substituted $(C_{1-6})$alkyl; hydroxy $(C_{1-6})$alkyl; an amino group optionally N-substituted by one or two $(C_{1-6})$alkyl, formyl, $(C_{1-6})$alkylcarbonyl or $(C_{1-6})$alkylsulphonyl groups; or aminocarbonyl wherein the amino group is optionally substituted by $(C_{1-4})$alkyl;

$R^2$ is hydrogen, or $(C_{1-4})$alkyl, or together with $R^6$ forms Y as defined below; A is a group (i) or (ib):

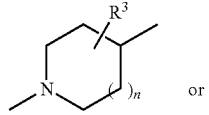

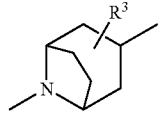

in which: $R^3$ is as defined for $R^{1a}$ or is oxo and n is 1 or 2: or A is a group (ii)

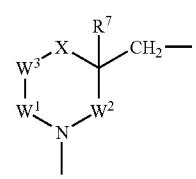

$W^1$, $W^2$ and $W^3$ are $CR^4R^8$ or $W^2$ and $W^3$ are $CR^4R^8$ and $W^1$ represents a bond between $W^3$ and N.

X is O, $CR^4R^8$, or $NR^6$;

one $R^4$ is as defined for $R^{1a}$ and the remainder and $R^8$ are hydrogen or one $R^4$ and $R^8$ are together oxo and the remainder are hydrogen;

$R^6$ is hydrogen or $(C_{1-6})$alkyl; or together with $R^2$ forms Y;

$R^7$ is hydrogen; halogen; hydroxy optionally substituted with $(C_{1-6})$alkyl; or $(C_{1-6})$alkyl;

Y is $CR^4R^8CH_2$; $CH_2CR^4R^8$; (C=O); $CR^4R^8$; $CR^4R^8$(C=O); or (C=O)$CR^4R^8$;

or when X is $CR^4R^8$, $R^8$ and $R^7$ together represent a bond;

U is selected from CO, and $CH_2$ and $R^5$ is an optionally substituted bicyclic carbocyclic or heterocyclic ring system (B):

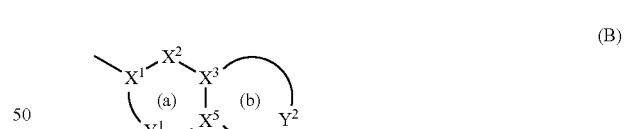

containing up to four heteroatoms in each ring in which at least one of rings (a) and (b) is aromatic;

$X^1$ is C or N when part of an aromatic ring, or $CR^{14}$ when part of a non-aromatic ring;

$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;

$X^3$ and $X^5$ are independently N or C;

$Y^1$ is a 0 to 4 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring;

$Y^2$ is a 2 to 6 atom linker group, each atom of $Y^2$ being independently selected from N, $NR^{13}$, O, $S(O)_x$, CO, $CR^{14}$ when part of an aromatic or non-aromatic ring or may additionally be $CR^{14}R^{15}$ when part of a non aromatic ring;

each of $R^{14}$ and $R^{15}$ is independently selected from: H; $(C_{1-4})$alkylthio; halo; carboxy$(C_{1-4})$alkyl; $(C_{1-4})$alkyl; $(C_{1-4})$alkoxycarbonyl; $(C_{1-4})$alkylcarbonyl; $(C_{1-4})$alkoxy $(C_{1-4})$alkyl; hydroxy; hydroxy$(C_{1-4})$alkyl; $(C_{1-4})$alkoxy; nitro; cyano; carboxy; amino or aminocarbonyl optionally mono- or di-substituted by $(C_{1-4})$alkyl; or $R^{14}$ and $R^{15}$ may together represent oxo;

each $R^{13}$ is independently H; trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; $(C_{1-4})$alkoxycarbonyl; $(C_{1-4})$alkylcarbonyl; $(C_{1-6})$alkylsulphonyl; aminocarbonyl wherein the amino group is optionally mono or disubstituted by $(C_{1-4})$alkyl;

each x is independently 0, 1 or 2; and $R^9$ is hydrogen or hydroxy.

This invention also provides a method of treatment of bacterial infections in mammals, particularly in man, which method comprises the administration to a mammal in need of such treatment an effective amount of a compound of formula (I), or a pharmaceutically acceptable salt, solvate and/or N-oxide thereof.

The invention also provides the use of a compound of formula (I), or a pharmaceutically acceptable salt, solvate and/or N-oxide thereof, in the manufacture of a medicament for use in the treatment of bacterial infections in mammals.

The invention also provides a pharmaceutical composition comprising a compound of formula (I), or a pharmaceutically acceptable salt, solvate and/or N-oxide thereof, and a pharmaceutically acceptable carrier.

DETAILED DESCRIPTION OF THE INVENTION

In a particular aspect $R^{1a}$ is hydrogen, $(C_{1-4})$alkoxy, $(C_{1-4})$alkylthio, $(C_{1-4})$alkyl, cyano, carboxy, hydroxymethyl or halogen; more particularly hydrogen, methoxy, methyl, cyano, or halogen.

In certain embodiments $R^{1a}$ is hydrogen, methoxy, methyl, or halogen, such as chloro or fluoro. In particular embodiments $R^{1a}$ is fluoro.

In a particular aspect $R^2$ is hydrogen.

Particular examples of $R^3$ include hydrogen; optionally substituted hydroxy; optionally substituted amino; halogen; $(C_{1-4})$ alkyl; 1-hydroxy-$(C_{1-4})$ alkyl; optionally substituted aminocarbonyl. More particular $R^3$ groups are hydrogen; $CONH_2$; 1-hydroxyalkyl e.g. $CH_2OH$; optionally substituted hydroxy e.g. methoxy; optionally substituted amino; and halogen, in particular fluoro. Most particularly $R^3$ is hydrogen, hydroxy or fluoro.

In a particular aspect, when A is (ia), n is 1. In a further aspect $R^3$ is in the 3- or 4-position. In a more particular aspect, A is (ia), n is 1 and $R^3$ is in the 3-position, and more particularly is cis to the $NR^2$ group.

In particular embodiments, A is a group (ia) in which n is 1 and $R^3$ is hydrogen or hydroxy.

In a particular aspect, when A is (ii), X is $CR^4R^8$ and $R^8$ is H or OH and more particularly OH is trans to $R^7$. In a further aspect $W^1$ is a bond. In another aspect $R^7$ is H. In particular embodiments $W^1$ is a bond, X, $W^2$ and $W^3$ are each $CH_2$ and $R^7$ is H.

In certain embodiments U is $CH_2$.

In certain embodiments $R^5$ is an aromatic heterocyclic ring (B) having 8-11 ring atoms including 2-4 heteroatoms of which at least one is N or $NR^{13}$ in which, in particular embodiments, $Y^2$ contains 2-3 heteroatoms, one of which is S and 1-2 are N, with one N bonded to $X^3$.

In alternative embodiments the heterocyclic ring (B) has ring (a) aromatic selected from optionally substituted benzo, pyrido and pyridazino and ring (b) non aromatic and $Y^2$ has 3-5 atoms, more particularly 4 atoms, including at least one heteroatom, more particularly one or two, with O, S, $CH_2$ or $NR^{13}$ bonded to $X^5$ where $R^{13}$ is other than hydrogen, and either NHCO bonded via N to $X^3$, or O, S, $CH_2$ or NH bonded to $X^3$. In a particular aspect the ring (a) contains aromatic nitrogen, and more particularly ring (a) is pyridine or pyridazine. Examples of rings (B) include optionally substituted:

(a) and (b) Aromatic 1H-pyrrolo[2,3-b]-pyridin-2-yl, 1H-pyrrolo[3,2-b]-pyridin-2-yl, 3H-imidazo[4,5-b]-pyrid-2-yl, 3H-quinazolin-4-one-2-yl, benzimidazol-2-yl, benzo[1,2,3]-thiadiazol-5-yl, benzo[1,2,5]-oxadiazol-5-yl, benzofur-2-yl, benzothiazol-2-yl, benzo[b]thiophen-2-yl (benzothiophen-2-yl), benzoxazol-2-yl, chromen-4-one-3-yl, imidazo[1,2-a]pyridin-2-yl, imidazo-[1,2-a]-pyrimidin-2-yl, indol-2-yl, indol-6-yl, isoquinolin-3-yl, [1,8]-naphthyridine-3-yl, oxazolo[4,5-b]-pyridin-2-yl, quinolin-2-yl, quinolin-3-yl, quinoxalin-2-yl, naphthalen-2-yl, 1,3-dioxo-isoindol-2-yl, benzimidazol-2-yl, 1H-benzotriazol-5-yl, 1H-indol-5-yl, 3H-benzooxazol-2-one-6-yl, 3H-benzooxazol-2-thione-6-yl, 3H-benzothiazol-2-one-5-yl, 3H-quinazolin-4-one-6-yl, pyrido[1,2-a]pyrimidin-4-one-3-yl (4-oxo-4H-pyrido[1,2-a]pyrimidin-3-yl), benzo[1,2,3]thiadiazol-6-yl, benzo[1,2,5]thiadiazol-5-yl, benzo[1,4]oxazin-2-one-3-yl, benzothiazol-5-yl, benzothiazol-6-yl, cinnolin-3-yl, imidazo[1,2-b]pyridazin-2-yl, pyrazolo[1,5-a]pyrazin-2-yl, pyrazolo[1,5-a]pyridin-2-yl, pyrazolo[1,5-a]pyrimidin-6-yl, pyrazolo[5,1-c][1,2,4]triazin-3-yl, pyrido[1,2-a]pyrimdin-4-one-2-yl (4-oxo-4H-pyrido[1,2-a]pyrimidin-2-yl), quinazolin-2-yl, quinoxalin-6-yl, thiazolo[3,2-a]pyrimidin-5-one-7-yl, thiazolo[5,4-b]pyridin-2-yl, thieno[3,2-b]pyridin-6-yl, thiazolo[5,4-b]pyridin-6-yl, thiazolo[4,5-b]pyridin-5-yl, [1,2,3]thiadiazolo[5,4-b]pyridin-6-yl, 2H-isoquinolin-1-one-3-yl (1-oxo-1,2-dihydro-isoquinolin-3-yl)

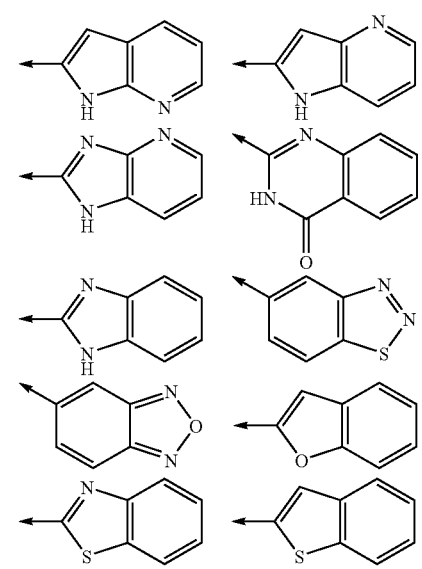

-continued
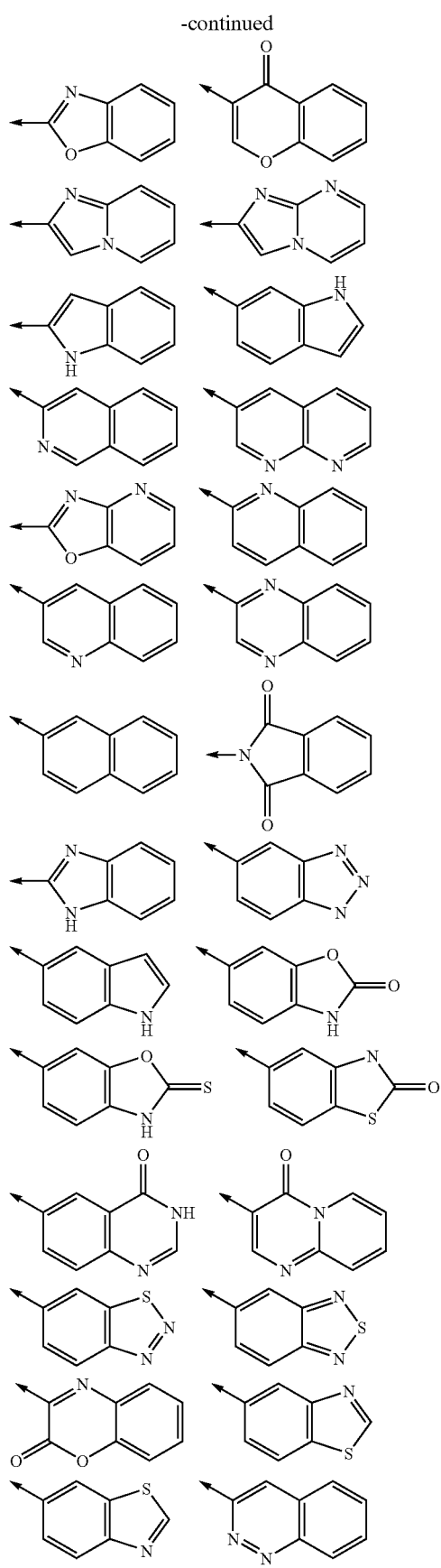
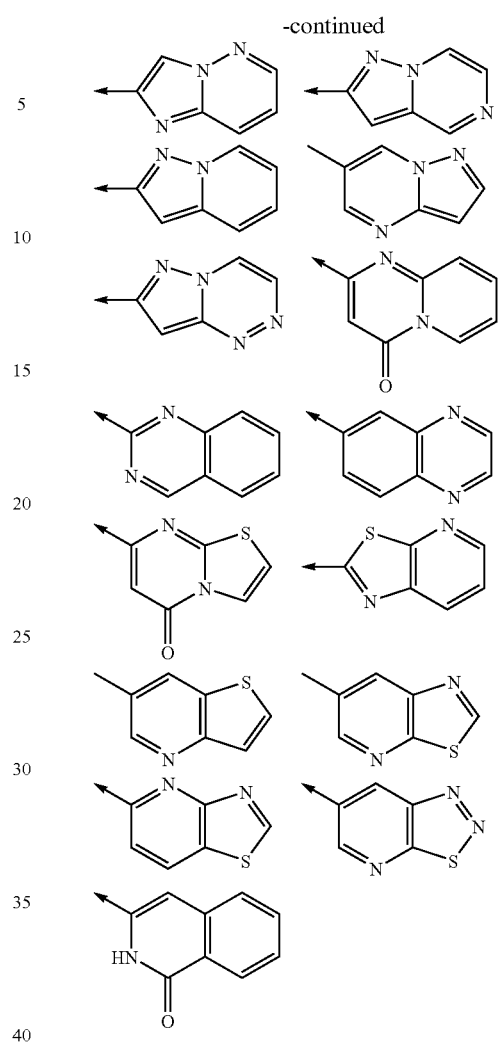
(a) is Non Aromatic
(2S)-2,3-dihydro-1H-indol-2-yl, (2S)-2,3-dihydro-benzo[1,4]dioxine-2-yl, 3-(R,S)-3,4-dihydro-2H-benzo[1,4]thiazin-3-yl, 3-(R)-2,3-dihydro-[1,4]dioxino[2,3-b]pyridin-3-yl, 3-(S)-2,3-dihydro-[1,4]dioxino[2,3-b]pyridin-3-yl, 2,3-dihydro-benzo[1,4]dioxan-2-yl, 3-substituted-3H-quinazolin-4-one-2-yl, indan-2-yl,
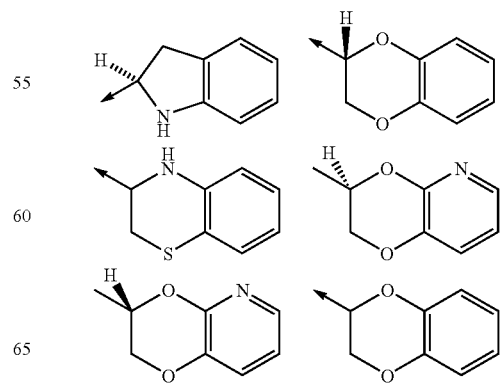

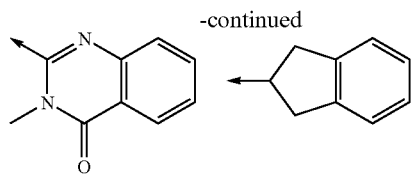

(b) is Non Aromatic 1,1,3-trioxo-1,2,3,4-tetrahydro1/⁶-benzo[1,4]thiazin-6-yl, benzo[1,3]dioxol-5-yl, 2,3-dihydro-benzo[1,4]dioxin-6-yl, 2-oxo-2,3-dihydro-benzooxazol-6-yl, 3-substituted-3H-benzooxazol-2-one-6-yl, 3-substituted-3H-benzooxazole-2-thione-6-yl, 3-substituted-3H-benzothiazol-2-one-6-yl, 4H-benzo[1,4]oxazin-3-one-6-yl (3-oxo-3,4-dihydro-2H-benzo[1,4]oxazin-6-yl), 4H-benzo[1,4]thiazin-3-one-6-yl (3-oxo-3,4-dihydro-2H-benzo[1,4]thiazin-6-yl), 4H-benzo[1,4]oxazin-3-one-7-yl, 4-oxo-2,3,4,5-tetrahydro-benzo[b][1,4]thiazepine-7-yl, 5-oxo-2,3-dihydro-5H-thiazolo[3,2-a]pyrimidin-6-yl, 1H-pyrido[2,3-b][1,4]thiazin-2-one-7-yl (2-oxo-2,3-dihydro-1H-pyrido[2,3-b]thiazin-7-yl), 2,3-dihydro-1H-pyrido[2,3-b][1,4]thiazin-7-yl, 2-oxo-2,3-dihydro-1H-pyrido[3,4-b]thiazin-7-yl, 2,3-dihydro-[1,4]dioxino[2,3-b]pyridin-6-yl, 2,3-dihydro-[1,4]dioxino[2,3-c]pyridin-7-yl, 2,3-dihydro-[1,4]dioxino[2,3-b]pyridin-7-yl, 3,4-dihydro-2H-benzo[1,4]oxazin-6-yl, 3,4-dihydro-2H-benzo[1,4]thiazin-6-yl, 3-oxo-3,4-dihydro-2H-pyrido[3,2-b][1,4]oxazin-6-yl, 3,4-dihydro-2H-pyrido[3,2-b][1,4]thiazin-6-yl, 3-oxo-3,4-dihydro-2H-pyrido[3,2-b][1,4]thiazin-6-yl, 3,4-dihydro-1H-quinolin-2-one-7-yl, 3,4-dihydro-1H-quinoxalin-2-one-7-yl, 6,7-dihydro-4H-pyrazolo[1,5-a]pyrimidin-5-one-2-yl, 5,6,7,8-tetrahydro-[1,8]naphthyridin-2-yl (1,2,3,4-tetrahydro-[1,8]naphthyridin-7-yl), 2-oxo-3,4-dihydro-1H-[1,8]naphthyridin-6-yl, 6-oxo-6,7-dihydro-5H-pyridazino[3,4-b][1,4]thiazin-3-yl (6-oxo-6,7-dihydro-5H-8-thia-1,2,5-triaza-naphthalen-3-yl), 2-oxo-2,3-dihydro-1H-pyrido[3,4-b][1,4]oxazin-7-yl, 2-oxo-2,3-dihydro-1H-pyrido[2,3-b][1,4]oxazin-7-yl, 6,7-dihydro-[1,4]dioxino[2,3-d]pyrimidin-2-yl, [1,3]oxathiolo[5,4-c]pyridin-6-yl, 3,4-dihydro-2H-pyrano[2,3-c]pyridine-6-yl, 2,3-dihydro[1,4]oxathiino[2,3-c]pyridine-7-yl, 2,3-dihydro-1-benzofuran-5-yl, 6,7-dihydro[1,4]oxathiino[2,3-c]pyridazin-3-yl, 6,7-dihydro[1,4]dioxino[2,3-c]pyridazin-3-yl, 2,3-dihydrofuro[2,3-c]pyridin-5-yl, 2,3-dihydro-1H-pyrido[3,4-b][1,4]oxazin-7-yl, 6,7-dihydro-5H-pyrano[2,3-c]pyridazin-3-yl, 1-oxo-1,2,3,4-tetrahydro-7-isoquinolinyl, 7-oxo-1,5,6,7-tetrahydropyrido[2,3-d]pyrimidin-2-yl, 6,7-dihydro-5H-pyrano[2,3-d]pyrimidin-2-yl.

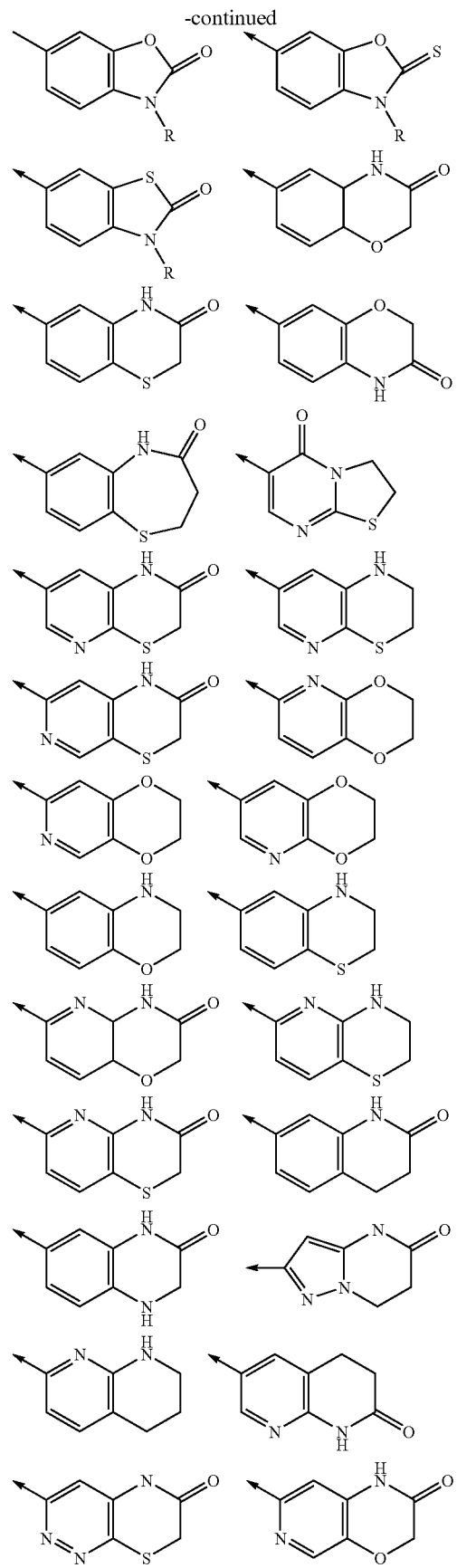

-continued

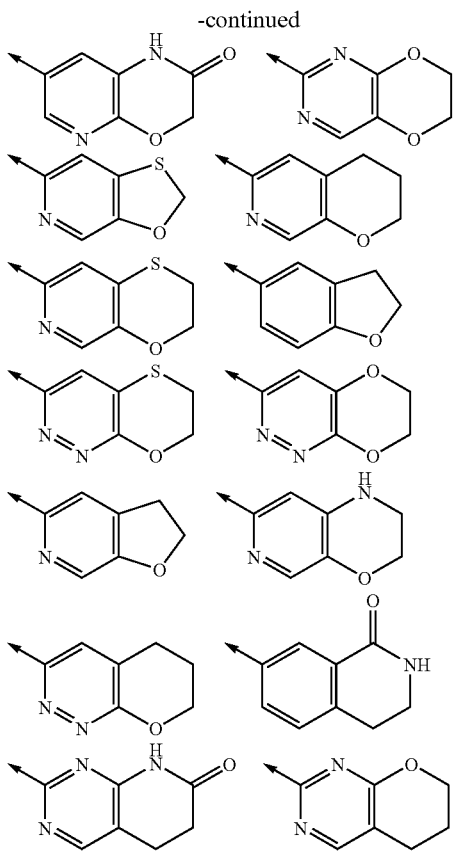

where R is an optional substituent

In some embodiments $R^{13}$ is H if in ring (a) or in addition $(C_{1-4})$alkyl such as methyl or isopropyl when in ring (b). More particularly, in ring (b) $R^{13}$ is H when $NR^{13}$ is bonded to $X^3$ and $(C_{1-4})$alkyl when $NR^{13}$ is bonded to $X^5$.

In further embodiments $R^{14}$ and $R^{15}$ are independently selected from hydrogen, halo, hydroxy, $(C_{1-4})$ alkyl, $(C_{1-4})$ alkoxy, nitro and cyano. More particularly $R^{15}$ is hydrogen.

More particularly each $R^{14}$ is selected from hydrogen, chloro, fluoro, hydroxy, methyl, methoxy, nitro and cyano. Still more particularly $R^{14}$ is selected from hydrogen, fluorine or nitro.

Most particularly $R^{14}$ and $R^{15}$ are each H.

Particular groups $R^5$ include:
[1,2,3]thiadiazolo[5,4-b]pyridin-6-yl
1H-pyrrolo[2,3-b]pyridin-2-yl
2,3-dihydro-[1,4]dioxino[2,3-b]pyridin-6-yl
2,3-dihydro-[1,4]dioxino[2,3-b]pyridin-7-yl
2,3-dihydro-[1,4]dioxino[2,3-c]pyridin-7-yl
2,3-dihydro-benzo[1,4]dioxin-6-yl
2-oxo-2,3-dihydro-1H-pyrido[2,3-b][1,4]oxazin-7-yl
2-oxo-2,3-dihydro-1H-pyrido[2,3-b][1,4]thiazin-7-yl
3,4-dihydro-2H-benzo[1,4]oxazin-6-yl
3-methyl-2-oxo-2,3-dihydro-benzooxazol-6-yl
3-oxo-3,4-dihydro-2H-benzo[1,4]oxazin-6-yl
3-oxo-3,4-dihydro-2H-pyrido[3,2-b][1,4]oxazin-6-yl
3-oxo-3,4-dihydro-2H-benzo[1,4]thiazin-6-yl (4H-benzo[1,4]thiazin-3-one-6-yl)
4-oxo-4H-pyrido[1,2-a]pyrimidin-2-yl
6-nitro-benzo[1,3]dioxol-5-yl
7-fluoro-3-oxo-3,4-dihydro-2H-benzo[1,4]oxazin-6-yl
8-hydroxy-1-oxo-1,2-dihydro-isoquinolin-3-yl
8-hydroxyquinolin-2-yl
benzo[1,2,3]thiadiazol-5-yl
benzo[1,2,5]thiadiazol-5-yl
benzothiazol-5-yl
thiazolo-[5,4-b]pyridin-6-yl
3-oxo-3,4-dihydro-2H-pyrido[3,2-b][1,4]thiazin-6-yl
7-chloro-3-oxo-3,4-dihydro-2H-pyrido[3,2-b][1,4]thiazin-6-yl
7-chloro-3-oxo-3,4-dihydro-2H-pyrido[3,2-b][1,4]oxazin-6-yl
7-fluoro-3-oxo-3,4-dihydro-2H-pyrido[3,2-b][1,4]thiazin-6-yl
2-oxo-2,3-dihydro-1H-pyrido[3,4-b][1,4]thiazin-7-yl
[1,3]oxathiolo[5,4-c]pyridin-6-yl
3,4-dihydro-2H-pyrano[2,3-c]pyridin-6-yl
5-carbonitro-2,3-dihydro-1,4-benzodioxin-7-yl (6-carbonitro-2,3-dihydro-1,4-benzodioxin-8-yl)
2,3-dihydro[1,4]oxathiino[2,3-c]pyridin-7-yl
5-fluoro-2,3-dihydro-1,4-benzodioxino-7-yl (8-fluoro-2,3-dihydro-1,4-benzodioxino-6-yl)
2,3-dihydro-1-benzofuran-5-yl
6,7-dihydro[1,4]oxathiino[2,3-c]pyridazin-3-yl
6,7-dihydro[1,4]dioxino[2,3-c]pyridazin-3-yl
2,3-dihydrofuro[2,3-c]pyridin-5-yl
2,3-dihydro-1H-pyrido[3,4-b][1,4]oxazin-7-yl
6,7-dihydro-5H-pyrano[2,3-c]pyridazin-3-yl
6-oxo-6,7-dihydro-5H-pyridazino[3,4-b][1,4]thiazin-3-yl
1-oxo-1,2,3,4-tetrahydro-7-isoquinolinyl
7-oxo-1,5,6,7-tetrahydropyrido[2,3-d]pyrimidin-2-yl
6,7-dihydro-5H-pyrano[2,3-d]pyrimidin-2-yl

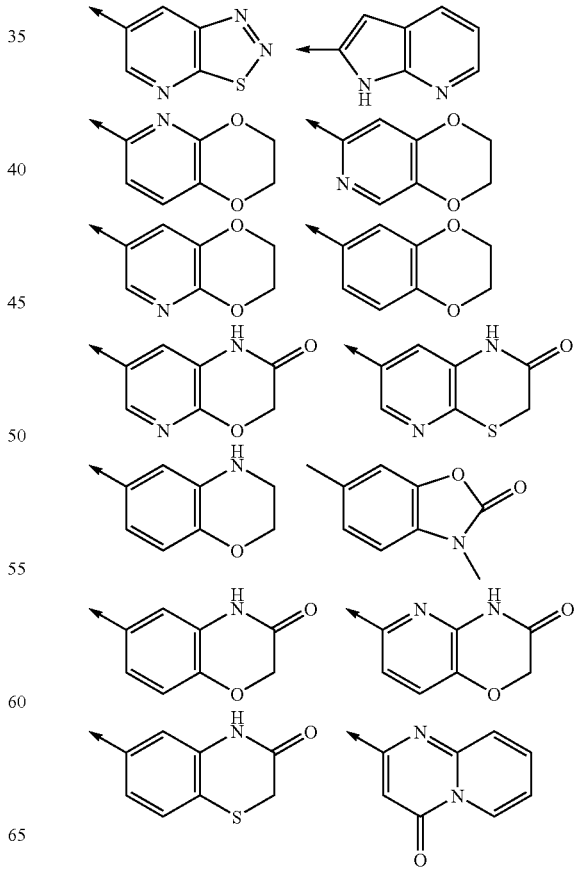

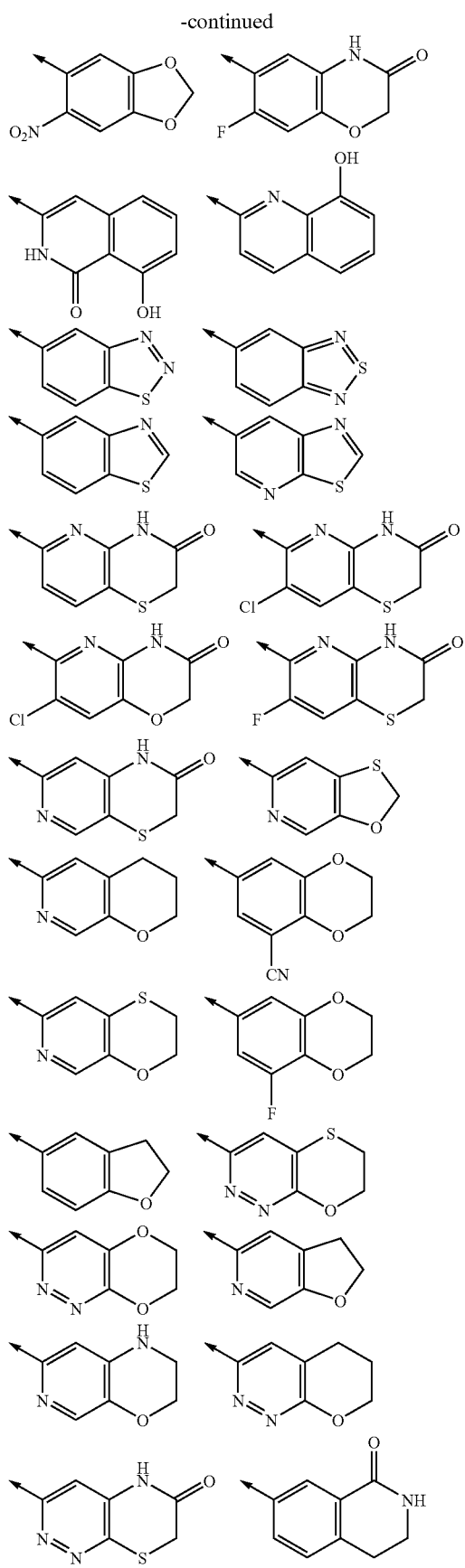

especially
3-oxo-3,4-dihydro-2H-pyrido[3,2-b][1,4]oxazin-6-yl
2,3-dihydrofuro[2,3-c]pyridin-5-yl
6,7-Dihydro[1,4]dioxino[2,3-c]pyridazin-3-yl
6,7-dihydro[1,4]oxathiino[2,3-c]pyridazin-3-yl
2,3-dihydro-[1,4]dioxino[2,3-c]pyridin-7-yl
[1,3]oxathiolo[5,4-c]pyridin-6-yl When used herein, the term "alkyl" includes groups having straight and branched chains, for instance, methyl, ethyl, n-propyl, iso-propyl, n-butyl, iso-butyl, sec-butyl, t-butyl, pentyl and hexyl. The term 'alkenyl' should be interpreted accordingly.

Halo or halogen includes fluoro, chloro, bromo and iodo.

Haloalkyl moieties include 1-3 halogen atoms.

Compounds within the invention contain a heterocyclyl group and may occur in two or more tautomeric forms depending on the nature of the heterocyclyl group; all such tautomeric forms are included within the scope of the invention.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Furthermore, it will be understood that phrases such as "a compound of formula (I) or a pharmaceutically acceptable salt, solvate or N-oxide thereof" are intended to encompass the compound of formula (I), an N-oxide of formula (I), a pharmaceutically acceptable salt of the compound of formula (I), a solvate of formula (I), or any pharmaceutically acceptable combination of these. Thus by way of non-limiting example used here for illustrative purpose, "a compound of formula (I) or a pharmaceutically acceptable salt or solvate thereof" may include a pharmaceutically acceptable salt of a compound of formula (I) that is further present as a solvate.

Since the compounds of formula (I) are intended for use in pharmaceutical compositions it will readily be understood that in particular embodiments they are provided in substantially pure form, for example at least 60% pure, more suitably at least 75% pure and particularly at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and more particularly from 10 to 59% of a compound of the formula (I) or pharmaceutically acceptable salt, solvate and/or N-oxide thereof.

Particular compounds according to the invention include those mentioned in the examples and their pharmaceutically acceptable N-oxides, salts and solvates.

Pharmaceutically acceptable salts of the above-mentioned compounds of formula (I) include the acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. Compounds of formula (I) may also be prepared as the N-oxide. The invention extends to all such derivatives.

Certain of the compounds of formula (I) may exist in the form of optical isomers, e.g. diastereoisomers and mixtures of isomers in all ratios, e.g. racemic mixtures. The invention includes all such forms, in particular the pure isomeric forms. For example the invention includes enantiomers and diastereoisomers at the attachment points of $NR^2$, $R^3$ and/or $R^9$. The different isomeric forms may be separated or resolved one from the other by conventional methods, or any given isomer may be obtained by conventional synthetic methods or by stereospecific or asymmetric syntheses.

In a further aspect of the invention there is provided a process for preparing compounds of formula (I) in which $R^9$ is H, and pharmaceutically acceptable salts, solvates and/or N-oxides thereof, which process comprises cyclising a compound of formula (IIA):

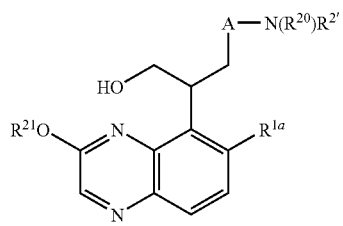

(IIA)

in which $R^{21}$ is $(C_{1-6})$alkyl, $R^{20}$ is $UR^5$ or a group convertible thereto and $R^{2'}$ is $R^2$ or a group convertible thereto, wherein A, $R^{1a}$, $R^2$, U and $R^5$ are as defined in formula (I), to give a compound of formula (IIB):

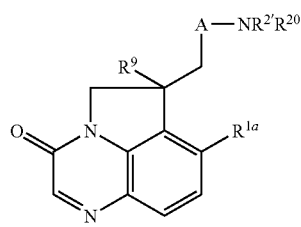

(IIB)

in which $R^9$ is H, and thereafter optionally or as necessary converting $R^{20}$ and $R^{2'}$ to $UR^5$ and $R^2$, interconverting any variable groups, and/or forming a pharmaceutically acceptable salt, solvate or N-oxide thereof.

The cyclisation reaction is effected by treatment of the compound of formula (IIA) with an activating agent such as methanesulphonyl chloride, p-toluenesulphonyl chloride, methanesulfonic anhydride or p-toluene sulfonic anhydride and an organic base such as triethylamine or diisopropylethylamine. Mesylate or tosylate preparation takes place under standard conditions and the compound of formula (IIB) forms in situ. Examples of $R^{21}$ include $(C_{1-4})$alkyl such as methyl.

In a further aspect of the invention there is provided a process for preparing compounds of formula (I) in which $R^9$ is OH, and pharmaceutically acceptable salts, solvates and/or N-oxides thereof, which process comprises cyclising a compound of formula (IIC):

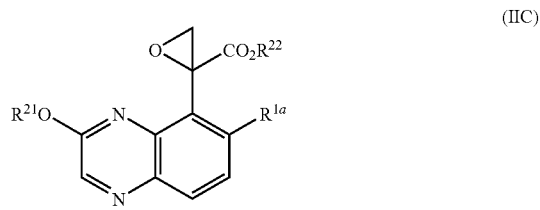

(IIC)

in which $R^{21}$ is $(C_{1-6})$alkyl such as methyl, $R^{22}$ is H or $(C_{1-6})$ alkyl such as methyl and $R^{1a}$ is as defined in formula (I), to give a compound of formula (IID):

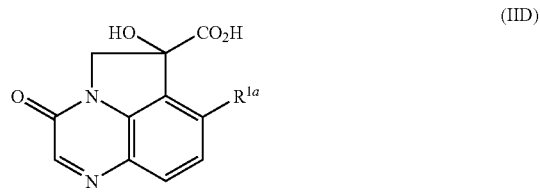

(IID)

and thereafter converting —$CO_2H$ to —$CH_2$-A-$NR^2$—$UR^5$, interconverting any variable groups, and/or forming a pharmaceutically acceptable salt, solvate or N-oxide thereof.

The cyclisation reaction may be effected by treatment of the compound of formula (IIC) with lithium hydroxide in water to give the tricyclic hydroxy-carboxylic acid (IID). Conversion of —$CO_2H$ to —$CH_2$-A-$NR^2$—$UR^5$ may be effected by methylation using methanol in sulphuric acid, followed by reduction to the diol with sodium borohydride in methanol, oxidation of the resulting tetrahydropyrroloquinoxalinone ring with manganese (IV) oxide and conversion to the tosyl derivative with tosyl chloride/dibutyltin oxide. Reaction with amine HN-A-$NR^{20}R^{2'}R^{20}$ where $R^{20}$ is $UR^5$ or a group convertible thereto and $R^{2'}$ is $R^2$ or a group convertible thereto, gives a compound of formula (IIB) in which $R^9$ is OH.

Conveniently one of $R^{20}$ and $R^{2'}$ is an N-protecting group, such as such as t-butoxycarbonyl, benzyloxycarbonyl or 9-fluorenylmethyloxycarbonyl. This may be removed by several methods well known to those skilled in the art (for examples see "*Protective Groups in Organic Synthesis*, T. W. Greene and P. G. M. Wuts, Wiley-Interscience, 1999), for example conventional acid hydrolysis with, for example trifluoroacetic acid or hydrochloric acid. The invention further provides compounds of formula (IIB) in which $R^{20}$ is hydrogen.

The free amine of formula (IIB) in which $R^{20}$ is hydrogen may be converted to $NR^2UR^5$ by conventional means such as amide formation with an acyl derivative $R^5COW$, for compounds where U is CO or, where U is $CH_2$, by alkylation with an alkyl halide $R^5CH_2$-halide in the presence of base, acylation/reduction with an acyl derivative $R^5COW$ or reductive alkylation with an aldehyde $R^5CHO$ under conventional conditions (see for examples Smith, M. B.; March, J. M. *Advanced Organic Chemistry*, Wiley-Interscience). The appropriate reagents containing the required $R^5$ group are known compounds or may be prepared analogously to known compounds, see for example WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO06002047, WO06014580, WO06010040, WO06017326, WO06012396, WO06017468, WO06020561 and EP0559285.

Where $R^5$ contains an NH group, this may be protected with a suitable N-protecting group such as t-butoxycarbonyl, benzyloxycarbonyl or 9-fluorenylmethyloxycarbonyl during the coupling of the $R^5$ derivative with the free amine of formula (IIB). The protecting group may be removed by conventional methods, such as by treatment with trifluoroacetic acid.

Conveniently the resolution of enantiomers at the attachment position of $R^9$ is carried out on the compound of formula (IIB), by any conventional method such as preparative high performance liquid chromatography.

The compound of formula (IIA) may be prepared by the following Scheme 1:

Scheme 1

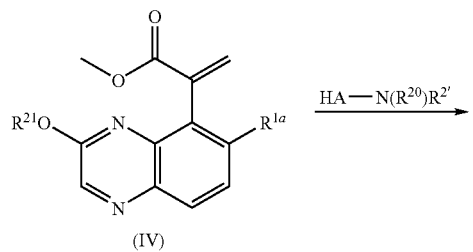

(IV)

-continued

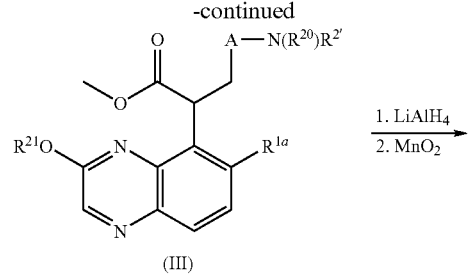

(III)

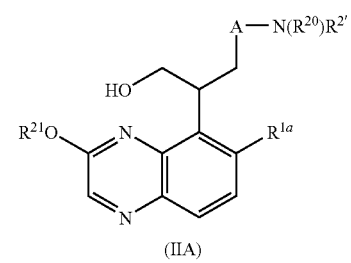

(IIA)

Compounds of general structure (III) may be prepared by reaction of acrylate ester (IV) with a compound $HA-N(R^{20})R^2$, such as a Boc protected amino-piperidine, under conventional conditions for Michael additions (see for examples Smith, M. B.; March, J. M. *Advanced Organic Chemistry*, Wiley-Interscience). Reduction of (III) to (IIA) occurs upon treatment with lithium aluminium hydride under conventional conditions. The reduction step may produce some dihydroquinoxaline compound which can be reoxidised to the desired compound of formula (IIA) with, for example, $MnO_2$ under conventional conditions (for examples of these reactions, see Smith, M. B.; March, J. M. *Advanced Organic Chemistry*, Wiley-Interscience).

The compound of formula (IIC) may be prepared by conventional epoxidation of the vinyl ester (IV) e.g. by oxidation with t-butyl hydrogen peroxide and potassium t-butoxide in THF.

A route to intermediate (IV) is shown in Scheme 2:

Scheme 2

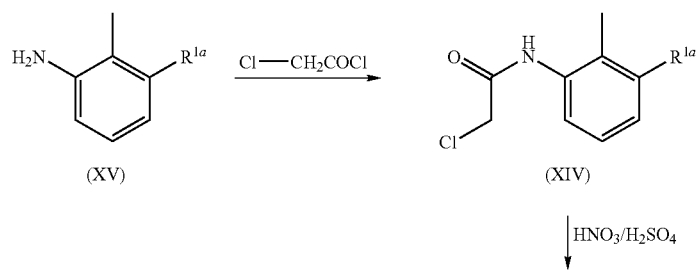

-continued

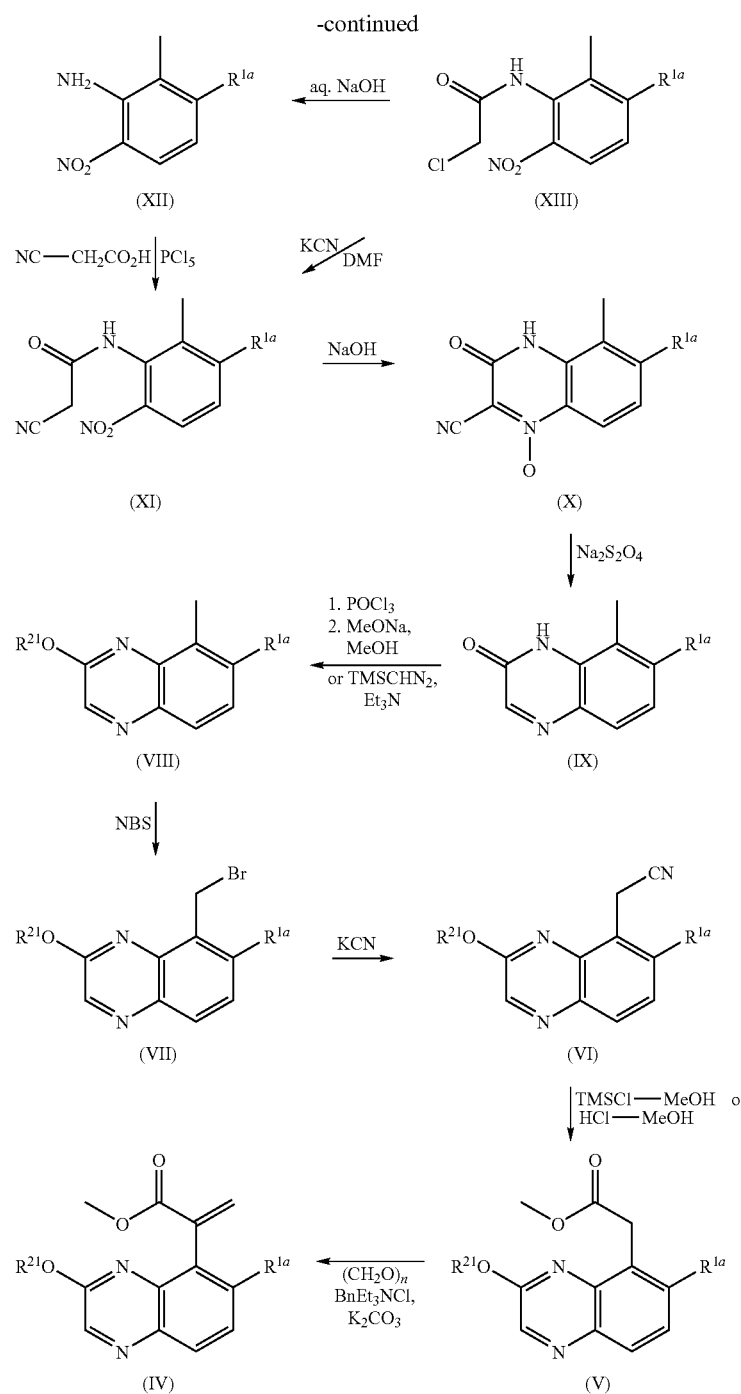

NBS = N-bromosuccinimide
TMSCl = chlorotrimethylsilane
TMSCHN₂ = (trimethylsilyl)diazomethane The fluoro-aniline (XV) is converted by acylation to the chloroacetamide (XIV), which is nitrated to give (XIII) and then hydrolysed to give the nitroaniline (XII). This is converted into the cyanoacetamide (XI) by treatment with cyanoacetic acid and phosphorus pentachloride (by the method of S. T. Hazeldine et al, J. Med. Chem., 2002, 44, 1758). Alternatively, the nitro-chloroacetamide (XIII) may be treated with potassium cyanide to give cyanoacetamide (XI) directly. Cyclisation with sodium hydroxide in pyridine gives a cyanoquinoxalinone-N-oxide (X) which is reduced by sodium dithionite with loss of the cyano group to give a compound of formula (IX). This is first chlorinated with phosphorus oxychloride and then treated with sodium methoxide or (IX) can be methylated with (trimethylsilyl)diazomethane in the presence of triethylamine and the methyl group functionalised with N-bromosuccinimide to give the bromomethyl analogue (VII). This is converted to the nitrile (VI) which undergoes acid-catalysed methanolysis (TMSCl or HCl in methanol) to the methyl ester (V), and then vinylation with paraformaldehyde. Some demethylated material is formed with (V), but this can be re-methylated with TMS-diazomethane. This route is particularly suitable for $R^{1a}$=F.

Interconversions of $R^{1a}$, $R^2$, A and $R^5$ are conventional. In compounds which contain an optionally protected hydroxy group, suitable conventional hydroxy protecting groups which may be removed without disrupting the remainder of the molecule include acyl and alkylsilyl groups. N-protecting groups are removed by conventional methods.

Interconversion of $R^{1a}$ groups may be carried out conventionally, on compounds of formula (I) or (IIB). For example $R^{1a}$ methoxy is convertible to $R^{1a}$ hydroxy by treatment with lithium and diphenylphosphine (general method described in Ireland et al., *J. Amer. Chem. Soc.*, 1973, 7829) or HBr. Alkylation of the hydroxy group with a suitable alkyl derivative bearing a leaving group such as halide, yields $R^{1a}$ substituted alkoxy. $R^{1a}$ halogen is convertible to other $R^{1a}$ by conventional means, for example to hydroxy, alkylthiol (via thiol) and amino using metal catalysed coupling reactions, for example using copper as reviewed in Synlett (2003), 15, 2428-2439 and Angewandte Chemie, International Edition, 2003, 42(44), 5400-5449. $R^{1a}$ fluoro may be converted to methoxy by treatment with sodium methoxide in methanol. $R^{1a}$ halo such as bromo may be converted to cyano by treatment with copper (I) cyanide in N,N-dimethylformamide. $R^{1a}$ carboxy may be obtained by conventional hydrolysis of $R^{1a}$ cyano, and the carboxy converted to hydroxymethyl by conventional reduction.

Compounds of formula HA-N($R^{20}$)$R^{2'}$ and (V) are known compounds or may be prepared analogously to known compounds, see for example WO2004/035569, WO20041089947, WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO2003082835, WO2002026723, WO06002047, WO06014580, WO06002047 and WO06014580.

As shown in Scheme 3, the hydroxy-aminomethylpyrrolidines of formula (13) (HA-NH($R^{20}$), A is (ii), X is $CR^4R^8$, $W^1$ is a bond, $W^2$ and $W^3$ are both $CH_2$, $R^4$ and $R^7$ are H and $R^8$ is OH) can be prepared from doubly protected chiral intermediate (16) and separated by preparative HPLC. The benzyloxycarbonyl protecting group is removed by hydrogenation to give (15) and the amino function converted to a trifluoroacetamide (14). The t-butoxycarbonyl (Boc) protecting group is removed with HCl to give the pyrrolidine hydrochloride salt (13).

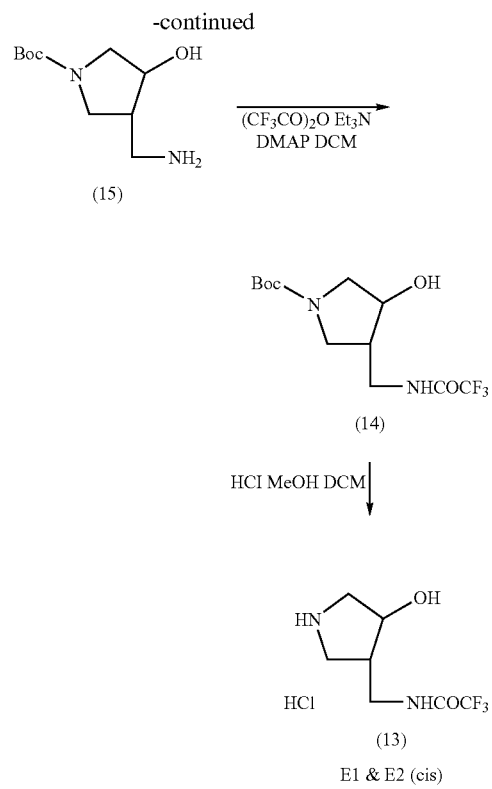

DMAP = 4-dimethylaminopyridine

The intermediate (16) may be prepared by the general method of Scheme 4:

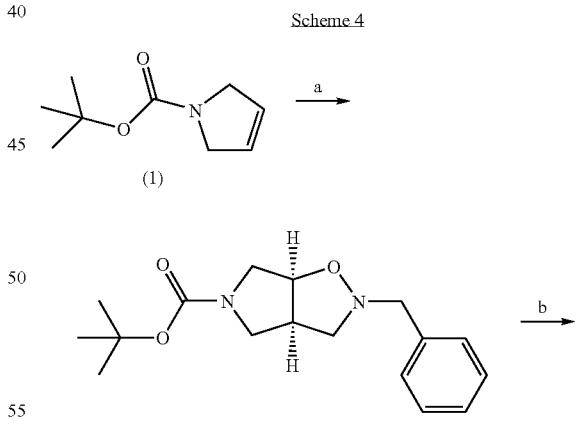

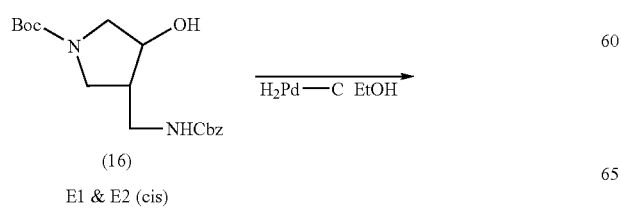

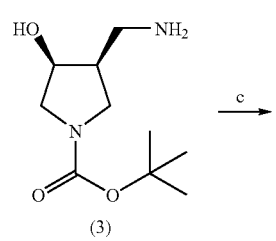

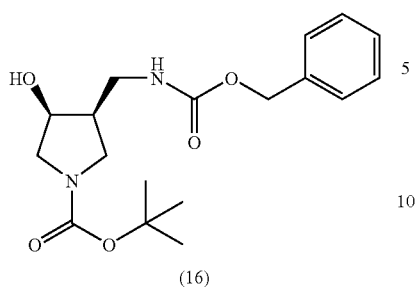

(16)

Reagents and conditions: (a) N-Hydroxybenzylamine hydrochloride, paraformaldehyde, toluene, ethanol, 80° C.; (b) Pd(OH)$_2$, H$_2$ (50 psi), MeOH, room temperature; (c) Benzyloxycarbonyl-succinimide, Et$_3$N, dichloromethane, room temperature.

In Scheme 5 the aminomethylpyrrolidine of formula (17) (HA-NH(R$^{20}$), A is (ii), X is CR$^4$R$^8$, W$^1$ is a bond, W$^2$ and W$^3$ are both CH$_2$, R$^4$, R$^7$ and R$^8$ are all H) can be prepared from commercially available Boc-protected aminomethylpyrrolidine, and converted to the trifluoroacetamide.

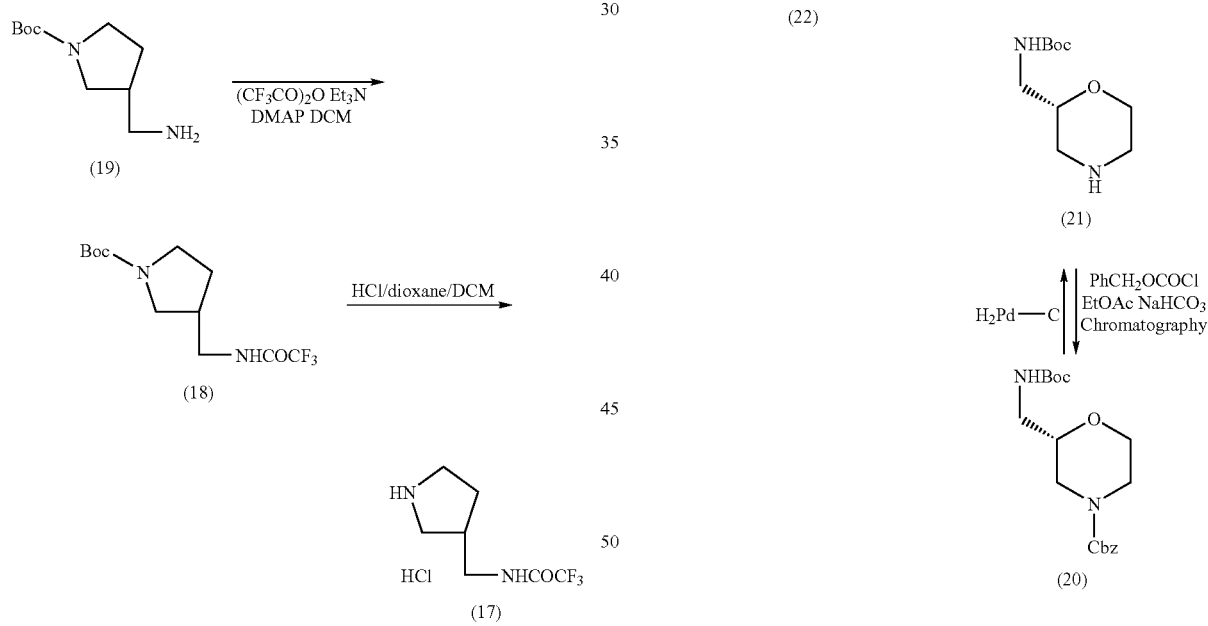

DMAP = 4-dimethylaminopyridine

The aminomethylmorpholine intermediate of formula (21) (HA-NH(R$^{20}$), A is (ii), X is O, W$^1$, W$^2$ and W$^3$ are each CH$_2$) may be prepared from a chiral dichlorobenzyl intermediate (23) (WO2003082835) (Scheme 6) by first protecting the amino function with a Boc-protecting group (22), removing the dichlorobenzyl group by hydrogenation to give (21), protecting the morpholine N-atom with a benzyloxycarbonyl group (to allow purification by chromatography) (20), and hydrogenation to afford the required morpholine derivative (21).

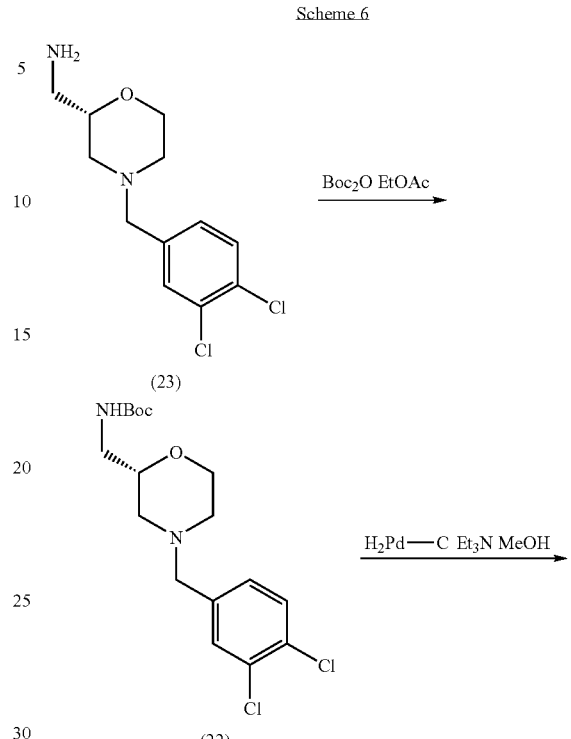

Further details for the preparation of compounds of formula (I) are found in the examples.

The antibacterial compounds according to the invention may be formulated for administration in any convenient way for use in human or veterinary medicine, by analogy with other antibacterials.

The pharmaceutical compositions of the invention include those in a form adapted for oral, topical or parenteral use and may be used for the treatment of bacterial infection in mammals including humans.

The composition may be formulated for administration by any route. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-1000 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 30 mg/kg per day.

The compound of formula (I) may be the sole therapeutic agent in the compositions of the invention or a combination with other antibacterials. If the other antibacterial is a β-lactam then a β-lactamase inhibitor may also be employed.

Compounds of formula (I) may be used in the treatment of bacterial infections caused by a wide range of organisms including both Gram-negative and Gram-positive organisms. Some compounds of formula (I) may be active against more than one organism. This may be determined by the methods described herein.

All publications, including but not limited to patents and patent applications, cited in this specification are herein incorporated by reference as if each individual publication were specifically and individually indicated to be incorporated by reference herein as though fully set forth.

The following examples illustrate the preparation of certain compounds of formula (I) and the activity of certain compounds of formula (I) against various bacterial organisms.

EXAMPLES AND EXPERIMENTAL

General

Abbreviations in the Examples

RT=room temperature

MS=mass spectrum

ES=Electrospray mass spectroscopy

LC/MS or LC-MS=Liquid chromatography mass spectroscopy

HPLC=High Performance Liquid Chromatography (Rt refers to retention time)

MDAP or Mass directed autoprep=mass directed preparative HPLC (using a ZQ mass spectrometer (Waters))

Certain reagents are also abbreviated herein. DMF refers to N,N-dimethylformamide, TFA refers to trifluoroacetic acid, THF refers to tetrahydrofuran, Pd/C refers to palladium on carbon catalyst, DCM refers to dichloromethane, MeOH refers to methanol.

Proton nuclear magnetic resonance ($^1$H NMR) spectra were recorded at 400 or 250 MHz, and chemical shifts are reported in parts per million (ppm) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, td=triplet of doublets, br=broad. CDCl$_3$ is deuteriochloroform. Mass spectra were obtained using electrospray (ES) ionization techniques. All temperatures are reported in degrees Celsius.

MP-carbonate refers to macroporous triethylammonium methylpolystyrene carbonate (Argonaut Technologies). Chiralpak AD and AD-H columns comprise of silica for preparative columns (5 um particle size AD-H 21 mm ID×250 mm L; 20 um particle size AD, 101.1 mm ID×250 mm L) coated with Amylose tris (3,5-dimethylphenylcarbamate) (Chiral Technologies USA. Measured retention times are dependent on the precise conditions of the chromatographic procedures. Where quoted below in the Examples they are indicative of the order of elution.

The preparation of triethenylboroxin.pyridine complex (2,4,6-trivinylcyclotriboroxane:pyridine complex) is described in Kerins, Fergal; O'Shea, Donal F. *J. Org. Chem.* (2002), 67(14), 4968.

Celite® is a filter aid composed of acid-washed diatomaceous silica, and is a trademark of Manville Corp., Denver, Colo.

As will be understood by the skilled chemist, references to preparations carried out in a similar manner to, or by the general method of, other preparations, may encompass variations in routine parameters such as time, temperature, workup conditions, minor changes in reagent amounts etc. Reactions involving metal hydrides including lithium hydride, lithium aluminium hydride, di-isobutylaluminium hydride, sodium hydride, sodium borohydride and sodium triacetoxyborohydride are carried out under argon.

Example 1

6-({4-[(2,3-Dihydro[1,4]dioxino[2,3-c]pyridin-7-ylmethyl)amino]-1-piperidinyl}methyl)-7-fluoro-5,6-dihydro-3H-pyrrolo[1,2,3-de]quinoxalin-3-one, Enantiomer E1 dihydrochloride

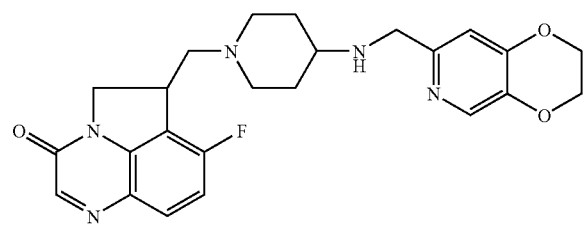

(a) 2-Chloro-N-(3-fluoro-2-methylphenyl)acetamide

A solution of chloroacetyl chloride (38.4 ml, 480 mmol) in ethyl acetate (100 ml) was slowly added to a vigorously-stirred mixture of 3-fluoro-2-methylaniline (60 g, 480 mmol), saturated aqueous sodium bicarbonate (400 ml), ice (ca 100 g) and ethyl acetate (400 ml). Some solid formed then dissolved. After 1 hour the mixture was evaporated to removing the ethyl acetate) and filtered, washing with water. The resulting product was dried in vacuo (94.4 g, 98%).

LC/MS (+ve ion electrospray): m/z 202/204 [MH$^+$]

(b) 2-Chloro-N-(3-fluoro-2-methyl-6-nitrophenyl)acetamide

A solution of 2-chloro-N-(3-fluoro-2-methylphenyl)acetamide (47.2 g, 234 mmol) in conc. sulphuric acid (220 ml) was treated at ca. −20° C. (ethanol/water/CO$_2$(s) bath) with conc. nitric acid (69%, 15.25 ml, 19 g, 235 mmol) over 30 minutes, keeping internal temperature ≦9° C. The reaction was complete at the end of the addition. The mixture was added to ice with vigorous stirring then left to stand overnight. Filtration, washing of the solid with water and drying afforded the product (54.6 g, 95%) containing ~9% impurity.

LC/MS (−ve ion electrospray): m/z 245/247 [(M−H$^+$)$^-$]

(c) 3-Fluoro-2-methyl-6-nitroaniline

2-Chloro-N-(3-fluoro-2-methyl-6-nitrophenyl)acetamide (prepared from 47.2 g of 2-chloro-N-(3-fluoro-2-methylphenyl)acetamide, ca. 234 mmol) was suspended in water (220 ml) then treated with aqueous sodium hydroxide solution (12.5M, 110 ml, 1.37 mol). Tetrahydrofuran (110 ml) was added, then the mixture was heated to reflux for 5 hours, then evaporated (removing most of the tetrahydrofuran). The yellow solid was filtered off and washed with water until washing were non-alkaline. Drying in vacuo afforded a yellow solid (32.3 g, 81% over 2 steps) containing ~13% isomer.

LC/MS (+ve ion electrospray): m/z 171 [MH$^+$]

(d) 2-Cyano-N-(3-fluoro-2-methyl-6-nitrophenyl)acetamide

Method A

To a solution of 3-fluoro-2-methyl-6-nitroaniline (10.0 g, 58.8 mmol) and cyanoacetic acid (10.1, 117.5 mmol) in dry toluene (500 ml) was added phosphorus pentachloride (25.8 g, 117.5 mmol) portionwise. The mixture was then heated at 120-125° C. while passing air over the mixture. After 2.5 h, an extra 1 g of cyanoacetic acid and 2.6 g phosphorus pentachloride were added and heating continued for 1 h, again while passing air over the mixture. After cooling, toluene was evaporated and the residue was dissolved in ethyl acetate and washed with brine, brine/sodium bicarbonate (twice) and brine, dried and evaporated. The crude product was recrystallised from ethanol, filtered, washed with ethanol/petrol (1:1) and dried to give product 10.72 g (77%), which contained some 6-fluoro-5-methyl-3-oxo-3,4-dihydro-2-quinoxalinecarbonitrile 1-oxide (lower-running yellow spot on TLC, 1:1 ethyl acetate/hexane).

Method B

2-Chloro-N-(3-fluoro-2-methyl-6-nitrophenyl)acetamide (2.7 g, 11 mmol) in dimethylformamide (20 ml) was treated with potassium cyanide (1.08 g, 16.6 mmol) and the mixture was stirred at room temperature for ~24 h. The dimethylformamide was evaporated and the residue was dissolved in ethyl acetate/water. The aqueous phase was extracted several times with ethyl acetate and the organic extracts were dried and evaporated. The crude product was recrystallised from ethanol/petrol (40-60° C.) to give a solid (1.44 g, 55%).

LC/MS (−ve ion electrospray): m/z 236 [(M−H$^+$)$^-$]

(e) 6-Fluoro-5-methyl-3-oxo-3,4-dihydro-2-quinoxalinecarbonitrile 1-oxide

2-Cyano-N-(3-fluoro-2-methyl-6-nitrophenyl)acetamide (11.17 g, 45 mmol) was mixed with in pyridine (50 ml) and 1M aqueous sodium hydroxide (46 ml) was added. The mixture was stirred at room temperature for ~24 h, then water was added to dissolve solids and the mixture was filtered, washing through with water. The filtrate (~300 ml) was acidified with 5M HCl to pH~6. The precipitate was filtered off, washed with water and dried to give 8.13 g of product. The filtrate was acidified to pH1 and extracted three times with ethyl acetate. The extracts were dried and evaporated and the residue was azeotroped twice with toluene to give 2.28 g product containing some of the acetamide starting material. Total yield 10.41 g, containing approx. 7% acetamide.

LC/MS (+ve ion electrospray): m/z 220 [MH$^+$]

(f) 7-Fluoro-8-methyl-2(1H)-quinoxalinone

A mixture of 6-fluoro-5-methyl-3-oxo-3,4-dihydro-2-quinoxalinecarbonitrile 1-oxide (15.9 g, 71.8 mmol) and sodium dithionite (36.7 g, 179.6 mmol) in ethanol (200 ml) and water (400 ml) was heated under reflux for 1 h, with a flow of argon over the top of the condenser leading to a bleach-filled bottle to trap HCN. The cooled mixture was carefully acidified to pH1 with dilute HCl and the mixture was stirred for 45 min at RT. Sodium hydroxide (50% aqueous) was then added to give pH~11 and the mixture was evaporated to remove approx. 500 ml. The residue was acidified to pH 6 with dilute HCl (caution: cyanide still present!) and the precipitate was filtered off, washed with water and dried to give a solid (10.37 g, 81%). Extraction of the aqueous liquor with 10% methanol/dichloromethane and evaporation of the extracts gave a further small amount of product (0.8 g). Total yield 11.2 g, 88%.

LC/MS (+ve ion electrospray): m/z 179 [MH$^+$]

(g) 2-Chloro-7-fluoro-8-methylquinoxaline

7-Fluoro-8-methyl-2(1H)-quinoxalinone (5.75 g, 32.3 mmol) in phosphorus oxychloride (30 ml) was heated under reflux for 2 h. Phosphorus oxychloride was removed by evaporation, and the residue was basified with aqueous sodium bicarbonate and extracted several times with ethyl acetate. The extracts were dried and evaporated, and the residue was dissolved in dichloromethane and passed quickly through a short column of silica (20 g), washing through with more dichloromethane. Removal of solvent gave product (4.13 g, 65%).

LC/MS (+ve ion electrospray): m/z 197/199 [MH$^+$]

(h) 7-Fluoro-8-methyl-2-(methyloxy)quinoxaline

2-Chloro-7-fluoro-8-methylquinoxaline (4.1 g, 20.9 mmol) was suspended in dry methanol and a 25% solution of sodium methoxide in methanol (4.73 ml, 21.9 mmol) was added by syringe. The mixture was heated under reflux for 2 h, then evaporated. The residue was dissolved in dichloromethane and water and the phases were separated. The aqueous phase was extracted twice with dichloromethane, and combined organic fractions were dried and evaporated to give product (3.84 g, 96%).

LC/MS (+ve ion electrospray): m/z 193 [MH$^+$]

(i) 8-Bromomethyl-7-fluoro-2-(methyloxy)quinoxaline

To 7-fluoro-8-methyl-2-(methyloxy)quinoxaline (50 g, 260 mmol) in dry chloroform (1 L) were added N-bromosuccinimide (52 g, 292 mmol) and benzoyl peroxide (70%, 0.42 g) and the mixture was heated under reflux, illuminated with a 120 W lamp, for 2 h. After cooling, the mixture was washed with water. The aqueous phase was re-extracted twice with dichloromethane and the combined organic fractions were washed with water, dried and evaporated to give product (72.1 g, 100%).

LC/MS (+ve ion electrospray): m/z 271/273 [MH$^+$]

(j) [6-Fluoro-3-(methyloxy)-5-quinoxalinyl]acetonitrile

A mixture of 8-bromomethyl-7-fluoro-2-(methyloxy)quinoxaline (5.89 g, 20 mmol) and potassium cyanide (3.2 g, 49 mmol) in dimethylformamide (125 ml) was heated at 50° C. for approx. 40 h. More potassium cyanide (0.8 g) was added and heating continued at 60° C. for ~8 h. The mixture was then evaporated and the residue was dissolved in dichloromethane and washed with water. The aqueous phase was extracted twice with dichloromethane and the combined organic fractions were dried and evaporated. Chromatography on silica (300 g), eluting with 0-25% ethyl acetate/hexane gave product (2.47 g, 57%).

LC/MS (+ve ion electrospray): m/z 218 [MH$^+$]

(k) Methyl [6-fluoro-3-(methyloxy)-5-quinoxalinyl]acetate

To a solution of [6-fluoro-3-(methyloxy)-5-quinoxalinyl] acetonitrile (1.47 g, 6.8 mmol) in anhydrous methanol (45 ml) was added chlorotrimethylsilane (2.53 ml, 19.9 mmol) by syringe. After heating at 70° C. overnight, a further 6.0 ml of chlorotrimethylsilane was added and heating was continued over the weekend. The mixture was concentrated to a small volume, the residue was basified with aqueous sodium bicarbonate and extracted three times with ethyl acetate. The extracts were dried and evaporated. Chromatography on silica (100 g), eluting with 0-5% methanol/dichloromethane, gave the ester (1.14 g, 67%), plus some recovered nitrile (0.36 g, 24%).

LC/MS (+ve ion electrospray): m/z 251 [MH$^+$]

(l) Methyl 2-[6-fluoro-3-(methyloxy)-5-quinoxalinyl]-2-propenoate

A mixture of methyl [6-fluoro-3-(methyloxy)-5-quinoxalinyl]acetate (7.2 g, 28.8 mmol), potassium carbonate (11.4 g), benzyl(triethyl)ammonium chloride (19.3 g) and paraformaldehyde (11.4 g) in cyclohexane (180 ml) was heated at 80° C. for ~26 h. After cooling, ethyl acetate and water were added and the phases were separated. The aqueous phase was extracted three times with ethyl acetate, and combined organic fractions were dried and evaporated. The crude product was chromatographed on silica (450 g), eluting with dichloromethane, to give the propenoate (6.76 g, 90%).

LC/MS (+ve ion electrospray): m/z 263 [MH$^+$]

(m) Methyl 3-[4-({[(1,1-dimethylethyl)oxy] carbonyl}amino)-1-piperidinyl]-2-[6-fluoro-3-(methyloxy)-5-quinoxalinyl]propanoate A mixture of methyl 2-[6-fluoro-3-(methyloxy)-5-quinoxalinyl]-2-propenoate (13.64 g, 52.1 mmol), 1,1-dimethylethyl 4-piperidinylcarbamate (11.45 g, 57.3 mmol) and 1,1,3,3-tetramethylguanidine (3.12 ml) in dry dimethylformamide (300 ml) was heated at 65° C. (bath temp.) for 17 h. The solvent was evaporated and the residue was dissolved in ethyl acetate and water. The aqueous phase was extracted twice with ethyl acetate and the combined organic fractions were dried and evaporated. Chromatography on silica (1000 g), eluting with 2-5% methanol/dichloromethane gave the product (21.81 g, 91%).

LC/MS (+ve ion electrospray): m/z 463 [MH$^+$]

(n) 1,1-Dimethylethyl (1-{2-[6-fluoro-3-(methyloxy)-5-quinoxalinyl]-3-hydroxypropyl}-4-piperidinyl)carbamate A solution of methyl 3-[4-({[(1,1-dimethylethyl)oxy] carbonyl}amino)-1-piperidinyl]-2-[6-fluoro-3-(methyloxy)-5-quinoxalinyl]propanoate (21.8 g, 47.2 mmol) in dry tetrahydrofuran (500 ml) was cooled in a CO$_2$(s)/acetonitrile/ water bath (−40 to −45° C.) and treated slowly with lithium aluminium hydride (1M in tetrahydrofuran, 76.2 ml). The mixture was stirred at −30 to −40° C. (internal temp.) for 7 h, with a further addition of lithium aluminium hydride (8 ml) after 5.5 h. Sodium hydroxide (2M) was added cautiously dropwise until a filterable precipitate was obtained. The mixture was diluted with ethyl acetate and filtered through kieselguhr, washed through with ethyl acetate and evaporated. The crude product was chromatographed on silica (1000 g), eluting with 0-6% methanol/dichloromethane to give the desired product (12.31 g), still containing some impurities, and later fractions containing a 1:1 mixture (7.58 g) of desired product and 1,1-dimethylethyl (1-{2-[6-fluoro-3-(methyloxy)-1,2-dihydro-5-quinoxalinyl]-3-hydroxypropyl}-4-piperidinyl)carbamate.

This 1:1 mixed material (7.58 g) was dissolved in dichloromethane (250 ml) and stirred with manganese(IV) oxide (15.6 g) at room temperature for 2.5 h. The mixture was filtered through kieselguhr, washed through with dichloromethane, and evaporated.

The residue was combined with the impure product obtained previously (12.31 g) and chromatographed on silica in two batches, 3 g on silica (100 g) eluting with 0-5% dichloromethane/methanol then the remainder on silica (750 g) eluting with 0-10% dichloromethane/methanol, and then mixed fractions from both columns on silica (100 g) eluting with 0-10% dichloromethane/methanol to give the product (10.7 g, 52% overall).

LC/MS (+ve ion electrospray): m/z 435 [MH$^+$]

(o) 1,1-Dimethylethyl {1-[(7-fluoro-3-oxo-5,6-dihydro-3H-pyrrolo[1,2,3-de]quinoxalin-6-yl)methyl]-4-piperidinyl}carbamate A mixture of 1,1-dimethylethyl (1-{2-[6-fluoro-3-(methyloxy)-5-quinoxalinyl]-3-hydroxypropyl}-4-piperidinyl)carbamate (10.8 g, 25 mmol), methanesulfonic anhydride (5.12 g, 28.7 mmol) and N,N-diisopropylethylamine (9.8 ml, 56 mmol) in dry chloroform (140 ml) was stirred at room temperature for 0.5 h, then heated under reflux for 3 days. The mixture was washed with aqueous sodium bicarbonate and the aqueous phase was extracted with dichloromethane. The combined organic fractions were dried and evaporated. The residue was chromatographed on silica (500 g), eluting with 0-5% methanol/dichloromethane to give the product (8.13 g, 81%).

LC/MS (+ve ion electrospray): m/z 403 [MH$^+$]

(p) 6-[(4-Amino-1-piperidinyl)methyl]-7-fluoro-5,6-dihydro-3H-pyrrolo[1,2,3-de]quinoxalin-3-one A solution of 1,1-dimethylethyl {1-[(7-fluoro-3-oxo-5,6-dihydro-3H-pyrrolo[1,2,3-de]quinoxalin-6-yl)methyl]-4-piperidinyl}carbamate (8.13 g, 20.2 mmol) in dichloromethane (150 ml) and methanol (100 ml) was cooled in iced water. Hydrogen chloride in 1,4-dioxane (4M, 160 ml) was added gradually, then the mixture was stirred for 1.5 h. The mixture was evaporated and the residue was triturated with ether and filtered off. The solid was partially dissolved in 25% methanol/dichloromethane (200 ml) and stirred with MP-carbonate (3.03 mmol/g, 27 g) for 1 h. The resin was filtered off, washed a few times with 10% methanol/dichloromethane and methanol alternately, and the filtrate was evaporated to give the product (5.96 g, 98%).

LC/MS (+ve ion electrospray): m/z 303 [MH$^+$]

(q) Title Compound

A solution of 6-[(4-Amino-1-piperidinyl)methyl]-7-fluoro-5,6-dihydro-3H-pyrrolo[1,2,3-de]quinoxalin-3-one (75% pure, 85 mg, 0.21 mmol) and 2,3-dihydro[1,4]dioxino[2,3-c]pyridine-7-carboxaldehyde (for a synthesis see WO2004058144 Example 2(c) or WO03/087098 Example 19(d)) (34 mg, 0.21 mmol) in chloroform/methanol (1:1, 6 ml) was heated under reflux for ~24 h. After cooling, sodium triacetoxyborohydride (147 mg, 0.69 mmol) was added and the mixture was stirred for ~5 h at room temperature. The mixture was washed with aqueous sodium bicarbonate and the aqueous phase was extracted three times with 10% methanol/dichloromethane. Combined organic fractions were dried and evaporated. Chromatography on a reverse-phase HPLC system with mass-directed collection (MDAP) (eluent acetonitrile/water/formic acid, with a very small amount of aqueous HCl added to assist dissolution of crude product in 1:1 DMSO/acetonitrile for injection, monitoring for m/z 452) gave the racemic formate salt (82 mg). This was treated with aqueous sodium bicarbonate and extracted three times with 10% methanol/dichloromethane. The extracts were dried and evaporated to give the racemic free base.

δH (d-4 methanol, 250 MHz) 1.44 (2H, m), 1.89 (2H, m), 2.09 (1H, td), 2.24 (1H, td), 2.50 (2H, m), 2.75 (1H, br d), 2.86 (1H, dd), 3.00 (1H, br d), 3.80 (2H, s), 4.02 (1H, m), 4.28 (2H, m), 4.33 (2H, m), 4.50 (2H, m), 6.83 (1H, s), 6.97 (1H, t), 7.68 (1H, dd), 8.11 (1H, s), 8.20 (1H, s).

LC/MS (+ve ion electrospray): m/z 452 [MH$^+$]

Racemic free-base (118 mg) was separated by chiral preparative HPLC using a Chiralpak AD-H® (5 u) column (21× 250 mm), eluting with acetonitrile/methanol/isopropylamine (50:50:0.1, 20 ml/min) to give the E1 isomer (55 mg), Rt 7.3 min, α$_D$+470 (0.1%, MeOH), ee>99%.

This was converted into the dihydrochloride salt by conventional methods.

Example 2

6-({4-[(2,3-dihydro[1,4]dioxino[2,3-c]pyridin-7-ylmethyl)amino]-1-piperidinyl}methyl)-7-fluoro-5, 6-dihydro-3H-pyrrolo[1,2,3-de]quinoxalin-3-one, Enantiomer E2 dihydrochloride

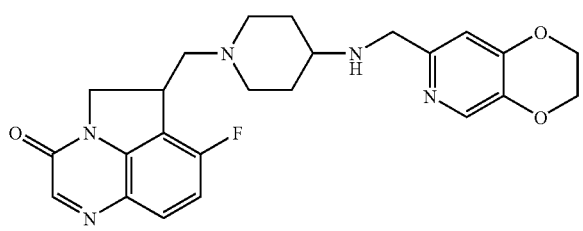

Racemic 6-({4-[(2,3-dihydro[1,4]dioxino[2,3-c]pyridin-7-ylmethyl)amino]-1-piperidinyl}methyl)-7-fluoro-5,6-dihydro-3H-pyrrolo[1,2,3-de]quinoxalin-3-one (118 mg) was separated by chiral preparative HPLC using a Chiralpak AD-H® (5 u) column (21×250 mm), eluting with acetonitrile/methanol/isopropylamine (50:50:0.1, 20 ml/min) to give the E2 isomer (55 mg), Rt 12.2 min, α$_D$−45° (0.1%, MeOH), ee>99%.

This was converted into the dihydrochloride salt by conventional methods.

Example 3

6-({4-[(6,7-Dihydro[1,4]dioxino[2,3-c]pyridazin-3-ylmethyl)amino]-1-piperidinyl}methyl)-7-fluoro-5,6-dihydro-3H-pyrrolo[1,2,3-de]quinoxalin-3-one dihydrochloride

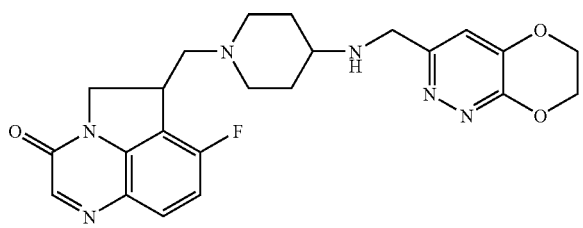

(a) 3,4,6-Trichloropyridazine

This was prepared by a slight variation on the method of Kasnar et al., Nucleosides & Nucleotides, (1994), 13(1-3), 459-79. Hydrazine sulphate salt (51 g) was suspended in water (250 ml), heated to reflux and bromomaleic anhydride (90.38 g) was added dropwise. The mixture was heated at reflux for 4 h then cooled to room temperature. The reaction was repeated with 29 g hydrazine sulphate, 53 g bromomaleic anhydride and 130 ml water. The precipitates were collected by filtration, washed with water and acetone and dried as a combined batch in vacuo to afford 4-bromo-1,2-dihydro-3,6-pyridazinedione as a white solid (113 g).

The solid in two batches was treated with phosphorus oxychloride (2×200 ml) and heated to reflux for 3.5 h. The mixture was cooled, evaporated and azeotroped with toluene. The residue was partitioned between dichloromethane and saturated aqueous sodium bicarbonate solution and extracted with DCM twice more. The organic extracts were dried and evaporated. This residue was re-dissolved in dichloromethane, and chromatographed on silica gel (300 g) (DCM as eluent) to give a white solid (101.5 g, 87%).

(LC/MS analysis showed ca. 20-30% impurity, isomers of bromo-dichloropyridazine).

MS (+ve ion electrospray) m/z 184/185/186 (MH+), trichloropyridazine

MS (+ve ion electrospray) m/z 228/229/231 (MH+), bromo-dichloropyridazine.

(b) 2-[(3,6-Dichloro-4-pyridazinyl)oxy]ethanol

A solution of ethylene glycol (55 ml) in tetrahydrofuran (200 ml) was treated at around 0° C. (ice bath cooling) with sodium hydride (60% dispersion in oil, 5.9 g) over 40 minutes. After the addition was complete, 3,4,6-trichloropyridazine (27 g) containing isomers of bromo-dichloropyridazine as impurity was added portionwise and washed in with more dry THF (50 ml) and the mixture was stirred at 0° C. for 1 hour and then at room temperature overnight. The mixture was concentrated (to ⅓ volume) then diluted with aqueous sodium bicarbonate solution and extracted with chloroform (5×) and ethyl acetate (3×). The combined organic extracts were washed with water, dried over sodium sulphate and evaporated and the solids filtered off and washed with CHCl$_3$ (×3) and dried in a vacuum oven overnight at 40° C. affording a white solid (25.5 g, 83%), containing some bromo-derivative (10-15%).

MS (+ve ion electrospray) m/z 209/211 (MH+).

MS (+ve ion electrospray) m/z 255/7 (MH+), bromo-derivative.

(c) 3-Chloro-6,7-dihydro[1,4]dioxino[2,3-c]pyridazine

A solution of 2-[(3,6-dichloro-4-pyridazinyl)oxy]ethanol containing some bromo-derivative (15.46 g; 0.0703 mol) in dry 1,4-dioxane (1.2 L) was treated with lithium hydride (2.3 g; 0.28 mol) in portions and stirred at room temperature for 1 hour under argon, then heated at 110° C. overnight. The reaction mixture was quenched with wet 1,4-dioxane, then iced-water. The solution was evaporated to half volume, taken to pH 8 with 5M hydrochloric acid and evaporated to dryness. Water was added and the. The residue was extracted 5× with chloroform, dried (sodium sulphate) and evaporated to afford a white solid (12.4 g, ca. 77%) (containing ca. 15% of a bromo species).

MS (+ve ion electrospray) m/z 173/5 (Cl MH$^+$); 217/9 (Br MH$^+$)

(d) 3-Ethenyl-6,7-dihydro[1,4]dioxino[2,3-c]pyridazine

A solution of 3-chloro-6,7-dihydro[1,4]dioxino[2,3-c]pyridazine (13.6 g, 0.079 mol) containing ca. 15% of a bromo species in dimethoxyethane (400 ml) was degassed under argon for 10 min then tetrakis(triphenylphosphine)palladium (0) (2 g), potassium carbonate (10.33 g), triethenylboroxin pyridine complex (11.32 g) and water (55 ml) were added. The mixture was heated at 95° C. for 48 h and cooled and evaporated to dryness. The mixture was treated with aqueous sodium bicarbonate solution and extracted (5×) with DCM. Extracts were dried (sodium sulphate), evaporated and the residue chromatographed on silica gel (500 g), eluting with 0-100% ethyl acetate-hexane, affording the product (6.43 g, 50%); [also some impure fractions (1.8 g)]

MS (+ve ion electrospray) m/z 165 (MH+).

(e) 6,7-Dihydro[1,4]dioxino[2,3-c]pyridazine-3-carbaldehyde

A solution of 3-ethenyl-6,7-dihydro[1,4]dioxino[2,3-c]pyridazine (11.58 g) in 1,4-dioxane/water (600 ml/180 ml), cooled in ice, was treated with an aqueous solution of osmium tetroxide (4% w/v, 25 ml) and sodium periodate (43 g). This mixture was allowed to warm to room temperature and after 7 h under stirring the mixture was evaporated to dryness and azeotroped with 1,4-dioxane. Silica gel, 1,4-dioxane and chloroform were added and the mixture was evaporated to dryness overnight, then added to a silica column (400 g) and chromatographed, eluting with chloroform then 0-100% ethyl acetate in hexane, to afford a white solid (7.55 g, 64%).

MS (+ve ion electrospray) m/z 167 (MH+).

(f) Title Compound

A solution of 6-[(4-amino-1-piperidinyl)methyl]-7-fluoro-5,6-dihydro-3H-pyrrolo[1,2,3-de]quinoxalin-3-one (95 mg, 0.31 mmol) and 6,7-dihydro[1,4]dioxino[2,3-c]pyridazine-3-carbaldehyde (52 mg, 0.31 mmol, 96% pure) in chloroform/methanol (1:1, 4 ml) was heated and stirred with 3 A molecular sieves at 80° C. for 18 h. After cooling, sodium triacetoxyborohydride (200 mg, 0.94 mmol) was added and the mixture was stirred for 6 h at room temperature. Further triacetoxyborohydride (100 mg) was added and the mixture was stirred for another 2 h. The mixture was quenched with aqueous sodium bicarbonate and the aqueous phase was extracted four times with 10% methanol/dichloromethane.

Combined organic fractions were dried (Na$_2$SO$_4$) and evaporated. Chromatography on silica (20 g), eluting with 0-20% methanol/dichloromethane gave the free base.

δH (CDCl$_3$, 400 MHz) 1.45 (2H, m), 1.91 (2H, m), 2.09 (1H, td), 2.24 (1H, td), 2.50 (1H, m), 2.58 (1H, m), 2.78 (1H, br d), 2.88 (1H, dd), 3.00 (1H, br d), 4.03 (2H, s+1H, m), 4.38 (2H, m), 4.50 (4H, m), 6.98 (1H, t), 7.06 (1H, s), 7.68 (1H, dd), 8.20 (1H, s)

LC/MS (+ve ion electrospray): m/z 453 [MH$^+$]

The free base in methanol/chloroform was treated with 4M hydrogen chloride in 1,4-dioxane and solvent was evaporated. The residue was triturated with ether and dried to give the dihydrochloride salt as a yellow solid (68 mg).

Example 4

6-({4-[(2,3-Dihydrofuro[2,3-c]pyridin-5-ylmethyl) amino]-1-piperidinyl}methyl)-7-fluoro-5,6-dihydro-3H-pyrrolo[1,2,3-de]quinoxalin-3-one dihydrochloride

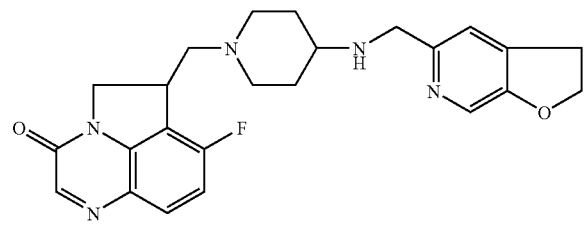

(a) {5-({[4-(Methyloxy)phenyl]methyl}oxy)-4-[(trimethylsilyl)ethynyl]-2-pyridinyl}methyl acetate (5-({[4-(Methyloxy)phenyl]methyl}oxy)-4-{[(trifluoromethyl)sulfonyl]oxy}-2-pyridinyl)methyl acetate (for a synthesis see WO2004058144 Example 60(d)) (10 g, 23 mmol) was dissolved in acetonitrile (400 ml) and triethylamine (65 ml) and copper (I) iodide (0.44 g, 2.3 mmol) were added. The mixture was degassed and placed under a blanket of argon. Trimethylsilylacetylene (10 ml, 69 mmol) and bis (triphenylphosphine)palladium(II) dichloride (0.645 g, 0.9 mmol) were added and the mixture heated to 45° C. for 18 h. The mixture was then allowed to cool and filtered. The filtrate was evaporated to dryness and the residue partitioned between ethyl acetate and water. The organic layer was separated and dried (sodium sulphate).

Chromatography on silica gel, eluting with a gradient of 20-75% ethyl acetate in 40-60° C. petroleum ether, gave an oil (8.45 g, 96%).

MS (+ve ion electrospray) m/z 384 (MH+).

(b) {5-Hydroxy-4-[(trimethylsilyl)ethynyl]-2-pyridinyl}methyl acetate, trifluoroacetate {5-({[4-(Methyloxy)phenyl]methyl}oxy)-4-[(trimethylsilyl)ethynyl]-2-pyridinyl}methyl acetate (8.45 g, 22 mmol) in dichloromethane (70 ml) was treated with trifluoroacetic acid (9.4 ml) and triethylsilane (3.33 ml) and stirred at ambient temperature for 18 h. The mixture was evaporated to dryness and chromatographed on silica gel, eluting with a gradient of 2-8% methanol in dichloromethane. This gave an oil (10 g, 100%).

MS (+ve ion electrospray) m/z 264 (MH+).

(c) Furo[2,3-c]pyridin-5-ylmethyl acetate

{5-Hydroxy-4-[(trimethylsilyl)ethynyl]-2-pyridinyl}methyl acetate, trifluoroacetate) (10 g, 22 mmol) was dissolved in pyridine (200 ml) and treated with copper(I) iodide (5.2 g, 27 mmol) then heated under reflux for 18 hrs. The mixture was allowed to cool, evaporated to dryness and the residue partitioned between ethyl acetate and water. This mixture was filtered through kieselguhr to remove copper residues. The organic layer was separated from the filtrate, dried and chromatographed on silica gel, eluting with a gradient of 10-60% ethyl acetate in 40-60° C. petroleum ether. This gave furo[2,3-c]pyridin-5-ylmethyl acetate (1.15 g, 27%) and a less polar product [2-(trimethylsilyl)furo[2,3-c]pyridin-5-yl]methyl acetate (1.3 g, 23%) as oils.

MS (+ve ion electrospray) m/z 192 (MH+) and MS (+ve ion electrospray) m/z 264 (MH+).

(d) Furo[2,3-c]pyridin-5-ylmethanol

A solution of furo[2,3-c]pyridin-5-ylmethyl acetate (1.15 g) in 1,4-dioxane (30 ml) and water (10 ml) was treated with 2M sodium hydroxide (12 ml) then stirred at ambient temperature for 18 h. The mixture was then partitioned between ethyl acetate and water. The organic fractions were separated and dried then evaporated to dryness. This gave an oil (0.63 g, 70%).

MS (+ve ion electrospray) m/z 150 (MH+).

(e) 2,3-Dihydrofuro[2,3-c]pyridin-5-ylmethanol

Furo[2,3-c]pyridin-5-ylmethanol (1.29 g, 8.7 mmol) was dissolved in ethanol (50 ml) and hydrogenated at RT, 1 atmosphere over 10% palladium on charcoal paste for 18 h. The mixture was filtered through kieselguhr and the filtrate evaporated to dryness, to give (1.31 g, 100%).

MS (+ve ion electrospray) m/z 152 (MH+).

(f) 2,3-Dihydrofuro[2,3-c]pyridine-5-carbaldehyde 2,3-Dihydrofuro[2,3-c]pyridin-5-ylmethanol (1.31 g, 8.7 mmol) was dissolved in dichloromethane (100 ml), treated with manganese (IV) dioxide (6 g, 69 mmol) and heated under reflux for 18 h. Filtration through kieselguhr and evaporation of the filtrate to dryness gave an oil (0.9 g, 70%).

MS (+ve ion electrospray) m/z 150 (MH+).

(g) Title Compound

A solution of 6-[(4-amino-1-piperidinyl)methyl]-7-fluoro-5,6-dihydro-3H-pyrrolo[1,2,3-de]quinoxalin-3-one (95 mg, 0.31 mmol) and 2,3-dihydrofuro[2,3-c]pyridine-5-carbaldehyde (46 mg, 0.31 mmol) in chloroform/methanol (1:1, 8 ml) was heated with 3 A molecular sieves under reflux overnight. After cooling, sodium triacetoxyborohydride (220 mg, 1.03 mmol) was added and the mixture was stirred for 6 h at room temperature. The mixture was washed with aqueous sodium bicarbonate and the aqueous phase was extracted four times with 10% methanol/dichloromethane. Combined organic fractions were dried and evaporated. Chromatography on silica, eluting with 0-20% methanol/dichloromethane gave the free base (75 mg, 56%).

δH (CDCl$_3$, 250 MHz) 1.46 (2H, m), 1.90 (2H, m), 2.10 (1H, td), 2.25 (1H, td), 2.48 (1H, m), 2.55 (1H, br m), 2.77 (1H, brd), 2.87 (1H, dd), 3.00 (1H, brd), 3.19 (2H, s), 3.86 (2H, s), 4.01 (1H, m), 4.51 (2H, m), 4.61 (2H, t), 6.97 (1H, t), 7.21 (1H, s), 7.68 (1H, dd), 8.08 (1H, s), 8.20 (1H, s).

LC/MS (+ve ion electrospray): m/z 436 [MH$^+$]

Example 5

6-({4-[(2,3-Dihydro[1,4]dioxino[2,3-b]pyridin-7-ylmethyl)amino]-1-piperidinyl}methyl)-7-fluoro-5,6-dihydro-3H-pyrrolo[1,2,3-de]quinoxalin-3-one dihydrochloride

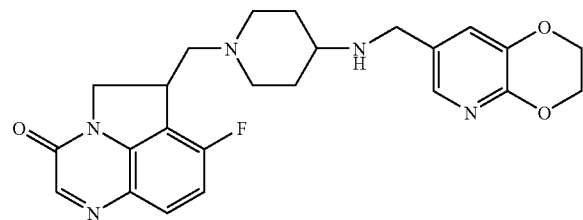

A solution of 6-[(4-amino-1-piperidinyl)methyl]-7-fluoro-5,6-dihydro-3H-pyrrolo[1,2,3-de]quinoxalin-3-one (95 mg, 0.31 mmol) and 2,3-dihydro[1,4]dioxino[2,3-b]pyridine-7-carbaldehyde (for a synthesis see WO03/087098 Example 20(e)) (50 mg, 0.31 mmol) in chloroform/methanol (1:1, 8 ml) was heated with 3 A molecular sieves under reflux overnight. After cooling, sodium triacetoxyborohydride (220 mg, 1.03 mmol) was added and the mixture was stirred for 6 h at room temperature. A further portion of borohydride (0.2 g) was added and heating continued for 3.5 h. The mixture was washed with aqueous sodium bicarbonate and the aqueous phase was extracted four times with 10% methanol/dichloromethane. Combined organic fractions were dried and evaporated. Chromatography on silica, eluting with 0-10% methanol/dichloromethane gave the free base (58 mg, 41%).

δH (CDCl$_3$, 250 MHz) 1.43 (2H, m), 1.88 (2H, m), 2.09 (1H, td), 2.23 (1H, td), 2.50 (2H, m), 2.75 (1H, brd), 2.87 (1H, dd), 3.00 (1H, brd), 3.74 (2H, s), 4.01 (1H, m), 4.24 (2H, m), 4.40 (2H, m), 4.47 (2H, m), 6.98 (1H, t), 7.21 (1H, d), 7.68 (1H, dd), 7.74 (1H, d), 8.20 (1H, s).

LC/MS (+ve ion electrospray): m/z 452 [MH$^+$]

The free base in methanol/chloroform was treated with two equivalents of 0.4M hydrogen chloride in 1,4-dioxane and solvent was evaporated to give the dihydrochloride salt (69 mg).

Example 6

7-Fluoro-6-[(4-{[(3-oxo-3,4-dihydro-2H-pyrido[3,2-b][1,4]oxazin-6-yl)methyl]amino}-1-piperidinyl)methyl]-5,6-dihydro-3H-pyrrolo[1,2,3-de]quinoxalin-3-one dihydrochloride

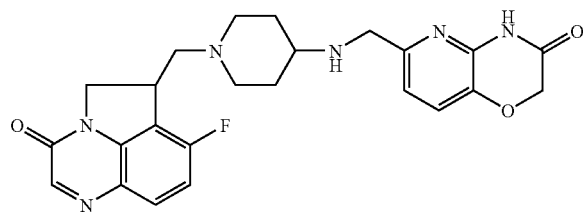

A solution of 6-[(4-amino-1-piperidinyl)methyl]-7-fluoro-5,6-dihydro-3H-pyrrolo[1,2,3-de]quinoxalin-3-one (95 mg, 0.31 mmol) and 3-oxo-3,4-dihydro-2H-pyrido[3,2-b][1,4]oxazine-6-carboxaldehyde (for a synthesis see WO03/087098 Example 31(e)) (55 mg, 0.31 mmol) in chloroform/methanol (1:1, 8 ml) was heated with 3 A molecular sieves under reflux overnight. After cooling, sodium triacetoxyborohydride (220 mg, 1.03 mmol) was added and the mixture was stirred for 6 h at room temperature. The mixture was washed with aqueous sodium bicarbonate and the aqueous phase was extracted four times with 10% methanol/dichloromethane. Combined organic fractions were dried and evaporated. Chromatography on silica, eluting with 0-10% methanol/dichloromethane gave the free base (102 mg, 71%).

δH (CDCl$_3$, 250 MHz) 1.46 (2H, m), 1.92 (2H, m), 2.10 (1H, td), 2.25 (1H, td), 2.51 (2H, m), 2.77 (1H, brd), 2.88 (1H, dd), 3.03 (1H, brd), 3.83 (2H, s), 4.02 (1H, m), 4.49 (2H, m), 4.64 (2H, s), 6.95 (1H, d), 6.98 (1H, t), 7.20 (1H, d), 7.67 (1H, dd), 8.20 (1H, s).

LC/MS (+ve ion electrospray): m/z 464 [MH$^+$]

The free base in methanol/chloroform was treated with two equivalents of 0.4M hydrogen chloride in 1,4-dioxane and solvent was evaporated to give the dihydrochloride salt (121 mg).

Example 7

7-Fluoro-6-[(4-{[(6-oxo-6,7-dihydro-5H-pyridazino[3,4-b][1,4]thiazin-3-yl)methyl]amino}-1-piperidinyl)methyl]-5,6-dihydro-3H-pyrrolo[1,2,3-de]quinoxalin-3-one dihydrochloride

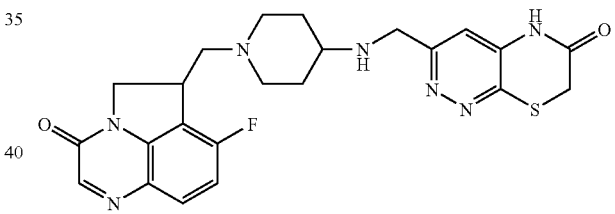

A solution of 6-[(4-amino-1-piperidinyl)methyl]-7-fluoro-5,6-dihydro-3H-pyrrolo[1,2,3-de]quinoxalin-3-one (48 mg, 0.16 mmol) and 6-oxo-6,7-dihydro-5H-pyridazino[3,4-b][1,4]thiazine-3-carboxaldehyde (for a synthesis see WO2004058144 Example 58) (50% pure, 63 mg, 0.16 mmol) in chloroform/methanol (1:1, 4 ml) was heated with 3 A molecular sieves under reflux overnight. After cooling, sodium triacetoxyborohydride (110 mg, 0.515 mmol) was added and the mixture was stirred for 5 h at room temperature. The mixture was washed with aqueous sodium bicarbonate and the aqueous phase was extracted several times with 10% methanol/dichloromethane. Combined organic fractions were dried and evaporated. Chromatography on a reverse-phase HPLC system with mass-directed collection (MDAP) (eluent acetonitrile/water/formic acid, monitoring for m/z 482) gave the formate salt (14 mg). This was treated with 4M hydrogen chloride in 1,4-dioxane and methanol, and solvent was evaporated to give the dihydrochloride salt (16 mg).

δH (d-4 methanol, 400 MHz) 2.30 (2H, m), 2.58 (2H, m), 3.58 (1H, m), 3.66 (4H, m), 3.73 (2H, m), 3.80 (1H, s), 3.84 (1H, m), 3.98 (1H, s), 4.07 (1H, m), 4.59 (2H, m), 4.63 (2H, s), 4.80 (1H, td), 7.13 (1H, s), 7.18 (1H, t), 7.83 (1H, dd), 8.17 (1H, s)

LC/MS (+ve ion electrospray): m/z 482 [MH$^+$]

Example 8

6-({4-[(2,3-Dihydro-1H-pyrido[3,4-b][1,4]oxazin-7-ylmethyl)amino]-1-piperidinyl}methyl)-7-fluoro-5,6-dihydro-3H-pyrrolo[1,2,3-de]quinoxalin-3-one dihydrochloride

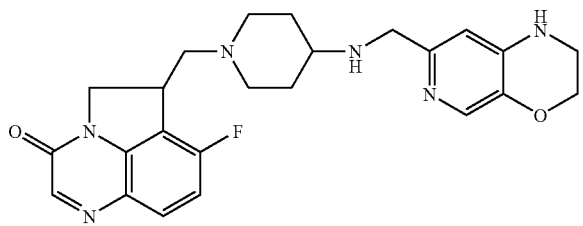

(a) {5-({[4-(Methyloxy)phenyl]methyl}oxy)-4-[(phenylmethyl)oxy]-2-pyridinyl}methyl acetate A solution of triphenylphosphine (39.3 g, 150 mmol) in tetrahydrofuran (600 ml) was treated at 0° C. with bis(1-methylethyl) (E)-1,2-diazenedicarboxylate (30 ml, 152 mmol). After 10 minutes [5-({[4-(methyloxy)phenyl]meth}oxy)-4-oxo-1,4-dihydro-2-pyridinyl]methyl acetate (33.5 g, 110 mmol) (for a synthesis, see WO2004058144, Example 60c) was added. After 10 minutes benzyl alcohol (13 g, 120 mmol) was added and the mixture was stirred overnight. Evaporation and chromatography on silica eluting with 20-40% ethyl acetate in hexane afforded an oil (26.3 g, 67%) (containing some triphenylphosphine oxide as an impurity).

MS (+ve ion electrospray) m/z 394 (MH+).

(b) {5-Hydroxy-4-[(phenylmethyl)oxy]-2-pyridinyl}methyl acetate trifluoroacetate salt A solution of {5-({[4-(methyloxy)phenyl]methyl}oxy)-4-[(phenyl methyl)oxy]-2-pyridinyl}methyl acetate (containing triphenylphosphine oxide as an impurity) (20 g, 50.8 mmol) in dichloromethane (500 ml) was treated with triethylsilane (10 ml, 62.6 mmol). A solution of trifluoroacetic acid (35 ml, 0.45 mol) in dichloromethane (200 ml) was added over 1 hour. After 2 hours the mixture was evaporated and chromatographed on silica gel eluting with 50-100% ethyl acetate-hexane, then 5-10% methanol-DCM affording a solid, the TFA salt in a 1:1 mixture with triphenylphosphine oxide (8.33 g).

MS (+ve ion electrospray) m/z 274 (MH+).

(c) (5-{[2-({[(1,1-Dimethylethyl)oxy]carbonyl}amino)ethyl]oxy}-4-{[(trifluoromethyl)sulfonyl]oxy}-2-pyridinyl)methyl acetate A solution of triphenylphosphine (24.1 g, 92 mmol) in tetrahydrofuran (600 ml) was treated at 0° C. with bis(1-methylethyl) (E)-1,2-diazenedicarboxylate (18.1 ml, 92 mmol). After 30 minutes a solution of 5-hydroxy-4-[(phenylmethyl)oxy]-2-pyridinyl}methyl acetate trifluoroacetate salt as a 1:1 mixture with triphenylphosphine oxide (23.8 g, 61.3 mmol) and triethylamine (8.6 ml, 61.3 mmol) in tetrahydrofuran (200 ml) was added. After 30 minutes the reaction was warmed to room temperature and left to stir for a further 30 minutes. 1,1-Dimethylethyl (2-hydroxyethyl)carbamate (9.5 ml, 61.3 mmol) was added and the mixture stirred overnight. Evaporation and chromatography on silica eluting with 0-100% ethyl acetate in petrol afforded an oil (40.2 g). The oil (40.2 g) was dissolved in ethanol (300 ml) and hydrogenated over 10% palladium on charcoal (20 g) for 16 hours. The mixture was filtered and evaporated to give a yellow oil (44.4 g).

A solution of the yellow oil (44.4 g) in dichloromethane (500 ml) was treated with triethylamine (9.41 ml) then 1,1,1-trifluoro-N-phenyl-N-[(trifluoromethyl)sulfonyl]methanesulfonamide (21.9 g). After 16 hours the mixture was washed with water, dried and evaporated. Chromatography on silica gel, eluting with 0-100% ethyl acetate in petrol afforded a colourless oil (19.7 g, 70%).

MS (+ve ion electrospray) m/z 459 (MH+).

(d) 1,1-Dimethylethyl 7-[(acetyloxy)methyl]-2,3-dihydro-1H-pyrido[3,4-b][1,4]oxazine-1-carboxylate A mixture of (5-{[2-({[(1,1-dimethylethyl)oxy]carbonyl}amino)ethyl]oxy}-4-{[(trifluoromethyl)sulfonyl]oxy}-2-pyridinyl)methyl acetate (1.58 g, 3.4 mmol), (±)-2,2'-bis(diphenylphosphino)-1,1'-binaphthalene (BI NAP) (110 mg, 0.2 mmol), palladium(II) acetate (25 mg, 0.1 mmol) and cesium carbonate (1.57 g, 4.8 mmol) in toluene (20 ml) was heated to 100° C. under argon for 16 hours then filtered and evaporated. (See S. L. Buchwald, Org Letts, 1999, 1, 35-37; for the procedure). The residue was chromatographed on silica gel, eluting with 0-100% ethyl acetate in petrol, to afford a white solid (0.84 g, 79%)

MS (+ve ion electrospray) m/z 309 (MH+).

(e) 1,1-Dimethylethyl 7-(hydroxymethyl)-2,3-dihydro-1H-pyrido[3,4-b][1,4]oxazine-1-carboxylate A solution of 1,1-dimethylethyl 7-[(acetyloxy)methyl]-2,3-dihydro-1H-pyrido[3,4-b][1,4]oxazine-1-carboxylate (0.84 g, 2.7 mmol) in 1,4-dioxane (20 ml) and water (5 ml) was treated with 2M sodium hydroxide solution (2.72 ml, 5.4 mmol). After 0.5 hour the mixture was concentrated to a volume of 5 ml and then partitioned between ethyl acetate and water. The organic extract was dried and evaporated to afford a colourless oil (0.78 g, 105%).

MS (+ve ion electrospray) m/z 267 (MH+).

(f) 1,1-Dimethylethyl 7-formyl-2,3-dihydro-1H-pyrido[3,4-b][1,4]oxazine-1-carboxylate A solution of 1,1-dimethylethyl 7-(hydroxymethyl)-2,3-dihydro-1H-pyrido[3,4-b][1,4]oxazine-1-carboxylate (0.78 g, 2.9 mmol) in dichloromethane (100 ml) was treated with manganese(IV) oxide (2.02 g, 23.3 mmol) and stirred overnight. Filtration and evaporation afforded a white solid (0.62 g, 81%).

MS (+ve ion electrospray) m/z 265 (MH+).

(g) 1,1-Dimethylethyl 7-[({1-[(7-fluoro-3-oxo-5,6-dihydro-3H-pyrrolo[1,2,3-de]quinoxalin-6-yl)methyl]-4-piperidinyl}amino)methyl]-2,3-dihydro-1H-pyrido[3,4-b][1,4]oxazine-1-carboxylate A solution of 6-[(4-amino-1-piperidinyl)methyl]-7-fluoro-5,6-dihydro-3H-pyrrolo[1,2,3-de]quinoxalin-3-one (95 mg, 0.31 mmol) and 1,1-dimethylethyl 7-formyl-2,3-dihydro-1H-pyrido[3,4-b][1,4]oxazine-1-carboxylate (83 mg, 0.31 mmol) in chloroform/methanol (1:1, 8 ml) was stirred with molecular sieves overnight, then heated under reflux for 3 h.

After cooling, sodium triacetoxyborohydride (164 mg) was added and the mixture was stirred for 5 h at room temperature. The mixture was basified and the aqueous phase was extracted with 10% methanol/dichloromethane. Combined organic fractions were dried and evaporated. Chromatography on silica, eluting with 0-20% (2M ammonia in methanol)/dichloromethane, gave impure material. Further chromatography on silica, eluting with 0-10% methanol/dichloromethane, gave the pure product (91 mg).

MS (+ve ion electrospray) m/z 551 (MH+).

(h) Title Compound 1,1-Dimethylethyl 7-[({1-[(7-fluoro-3-oxo-5,6-dihydro-3H-pyrrolo[1,2,3-de]quinoxalin-6-yl)methyl]-4-piperidinyl}amino)methyl]-2,3-dihydro-1H-pyrido[3,4-b][1,4]oxazine-1-carboxylate (91 mg, 0.165 mmol) in dichloromethane (2 ml) and methanol (1.5 ml) was treated with 4M hydrogen chloride in 1,4-dioxane (3.5 ml). After standing at room temperature for 2.5 h, the mixture was evaporated. The residue was triturated twice with ether and dried to give the title compound (89 mg).

δH (d-4 methanol, 400 MHz) 2.30 (2H, m), 2.58 (2H, m), 3.68 (4H, m), 3.77 (3H, m), 3.85 (1H, m), 4.07 (1H, m), 4.30 (2H, m), 4.47 (2H, s), 4.58 (2H, m), 4.80 (1H, td), 7.18 (1H, t), 7.23 (1H, s), 7.83 (1H, dd), 8.00 (1H, s), 8.17 (1H, s)

LC/MS (+ve ion electrospray): m/z 451 [MH$^+$]

Example 9

6-({4-[(2,3-Dihydro[1,4]dioxino[2,3-c]pyridin-7-ylmethyl)amino]-1-piperidinyl}methyl)-7-fluoro-6-hydroxy-5,6-dihydro-3H-pyrrolo[1,2,3-de]quinoxalin-3-one dihydrochloride

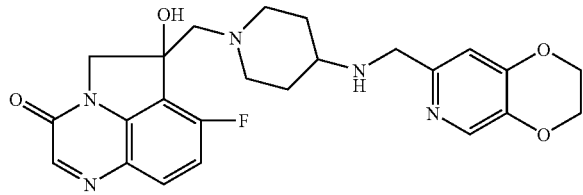

(a) 2-[6-Fluoro-3-(methyloxy)-5-quinoxalinyl]-2-oxiranecarboxylic acid

A solution of methyl 2-[6-fluoro-3-(methyloxy)-5-quinoxalinyl]-2-propenoate (5.45 g, 0.02 mol) (for a preparation, see Example 1(l)) in THF (150 ml) was cooled to 0° C. A 6M solution tert-butyl hydrogen peroxide in nonane (5.2 mL, 0.03 mol) was added dropwise followed by a 1M solution of potassium tert-butoxide (10.39 mL, 0.01 mol). During the addition the temperature was kept at 0° C. The reaction mixture was kept at 0° C. for 16 hours. Another 0.5 equivalent of the 1M solution of potassium tert-butoxide (10.39 mL, 0.01 mol) was added at 0° C. and the reaction mixture was kept for a further 2 hours. The reaction was quenched by addition of a 1M solution of HCl in methanol (20 mL). The reaction mixture was evaporated to dryness. The residue was partially dissolved in methanol. The organic layer was dried over magnesium sulphate, filtered, evaporated under vacuum and chromatographed on silica (required repeated chromatography), eluting with a 0-30% methanol in dichloromethane gradient to afford the product as a white solid (3.22 g, 59%)

MS (+ve ion electrospray) m/z 265 (MH+).

(b) 7-Fluoro-6-hydroxy-3-oxo-5,6-dihydro-3H-pyrrolo[1,2,3-de]quinoxaline-6-carboxylic acid A solution of 2-[6-fluoro-3-(methyloxy)-5-quinoxalinyl]-2-oxiranecarboxylic acid (3.22 g, 0.012 mol) in 1,4-dioxane (210 mL) and water (90 mL) was treated with lithium hydroxide (584 mg, 0.024 mol) dropwise at RT. The reaction mixture was heated at 80° C. for 35 hours then cooled, quenched to pH 7 with a 2M solution of hydrochloric acid and then the solvent was evaporated. The residue was placed directly onto a 100 g silica gel column and chromatographed, eluting with a 0-50% methanol in dichloromethane gradient to afford the product as a yellow solid (7.07 g of a 3:1 mixture of product/starting material).

MS (+ve ion electrospray) m/z 251 (MH+).

(c) Methyl 7-fluoro-6-hydroxy-3-oxo-5,6-dihydro-3H-pyrrolo[1,2,3-de]quinoxaline-6-carboxylate A 3:1 mixture of 7-fluoro-6-hydroxy-3-oxo-5,6-dihydro-3H-pyrrolo[1,2,3-de]quinoxaline-6-carboxylic acid and 2-[6-fluoro-3-(methyloxy)-5-quinoxalinyl]-2-oxiranecarboxylate (3.05 g) was partially dissolved in methanol (100 mL) and treated with concentrated sulphuric acid (1 mL), added dropwise at room temperature. The reaction mixture was stirred for 17 hours then quenched to pH 7 by addition of MP-carbonate resin. The mixture was filtered and evaporated. The residue was placed directly onto the top of a 100 g silica gel column and chromatographed, eluting with a 0-50% methanol in ethyl acetate gradient to afford the product (0.558 g, 17% (23% based on acid starting material).

MS (+ve ion electrospray) m/z 265 (MH+).

(d) 7-Fluoro-6-hydroxy-6-(hydroxymethyl)-1,2,5,6-tetrahydro-3H-pyrrolo[1,2,3-de]quinoxalin-3-one A solution of methyl 7-fluoro-6-hydroxy-3-oxo-5,6-dihydro-3H-pyrrolo[1,2,3-de]quinoxaline-6-carboxylate (0.558 g, 0.002 mol) in methanol (40 mL) was cooled to 0° C. and treated with sodium borohydride (0.080 g, 0.002 mol). After 2 hours and again after a further 2 hours, further portions of sodium borohydride (0.04 g, 0.5 equivalent each time) were added at 0° C. After 5 hours in total, the reaction mixture was quenched by addition of water (2 mL) and the solvent was removed. The residue was placed directly onto the top of a 20 g silica gel column and chromatographed, eluting with a 0-100% ethyl acetate in hexane gradient, then with a 0-50% methanol in ethyl acetate gradient to afford the product (0.331 g, 66%).

MS (+ve ion electrospray) m/z 239 (MH+).

(e) 7-Fluoro-6-hydroxy-6-(hydroxymethyl)-5,6-dihydro-3H-pyrrolo[1,2,3-de]quinoxalin-3-one A mixture of 7-fluoro-6-hydroxy-6-(hydroxymethyl)-1,2,5,6-tetrahydro-3H-pyrrolo[1,2,3-de]quinoxalin-3-one (0.331 g, 0.001 mol), and manganese (IV) oxide (1.84 g, 0.021 mol) in DMF (50 mL) was stirred at room temperature for 1 hour. The reaction mixture was filtered through Celite®, washed with methanol and the solvent was removed. The residue was placed directly onto the top of a 20 g silica gel column and chromatographed, eluting with a 0-100% ethyl acetate in hexane gradient, then with a 0-50% methanol in ethyl acetate gradient to afford the product (0.267 g, 81%).

MS (+ve ion electrospray) m/z 237 (MH+).

(f) (7-Fluoro-6-hydroxy-3-oxo-5,6-dihydro-3H-pyrrolo[1,2,3-de]quinoxalin-6-yl)methyl 4-methyl benzenesulfonate A mixture of 7-fluoro-6-hydroxy-6-(hydroxymethyl)-5,6-dihydro-3H-pyrrolo[1,2,3-de]quinoxalin-3-one (0.267 g, 0.0011 mol), 4-toluenesulfonyl chloride (0.216 g, 0.0011 mol), triethylamine (0.236 mL, 0.0014 mol) and dibutyltin oxide (0.014 g, 0.06 mmol) in dichloromethane (10 mL), THF (10 mL) and DMF (1 mL) was stirred at room temperature for 16 hours. The reaction mixture was worked up by addition of a saturated solution of sodium bicarbonate (20 mL) and dichloromethane (20 mL). The aqueous layer was washed further with dichloromethane (3×20 mL). The combined organic layers were dried over sodium sulphate, filtered and the solvent was removed. The crude mixture was chromatographed on 20 g of silica gel, eluting with a 0-100% ethyl acetate in petrol gradient, then with a 0-50% methanol in ethyl acetate gradient to afford the product (0.275 g, 62%).
MS (+ve ion electrospray) m/z 391 (MH+).

(g) 1,1-Dimethylethyl (2,3-dihydro[1,4]dioxino[2,3-c]pyridin-7-ylmethyl){1-[(7-fluoro-6-hydroxy-3-oxo-5,6-dihydro-3H-pyrrolo[1,2,3-de]quinoxalin-6-yl)methyl]-4-piperidinyl}carbamate To a mixture of (7-fluoro-6-hydroxy-3-oxo-5,6-dihydro-3H-pyrrolo[1,2,3-de]quinoxalin-6-yl)methyl 4-methylbenzenesulfonate (0.093 g, 0.24 mmol) in ethanol (3 mL) was added 1,1-dimethylethyl (2,3-dihydro[1,4]dioxino[2,3-c]pyridin-7-ylmethyl)4-piperidinylcarbamate (for a synthesis see WO 2004058144 Example 99(h)) (78.5 mg, 0.22 mmol), then sodium carbonate (71.5 mg, 0.68 mmol). The reaction mixture was stirred at room temperature for 16 hours and evaporated to dryness. The residue was placed directly onto the top of a 20 g silica gel column and chromatographed eluting with a 0-100% ethyl acetate in petrol gradient, then with a 0-50% methanol in ethyl acetate gradient to afford the product (70 mg, 52%).
MS (+ve ion electrospray) m/z 568 (MH+).

(h) Title Compound

A solution of 1,1-dimethylethyl (2,3-dihydro[1,4]dioxino[2,3-c]pyridin-7-ylmethyl){1-[(7-fluoro-6-hydroxy-3-oxo-5,6-dihydro-3H-pyrrolo[1,2,3-de]quinoxalin-6-yl)methyl]-4-piperidinyl}carbamate (133 mg, 0.234 mmol) in dichloromethane (10 mL) was treated with trifluoroacetic acid (2 mL) dropwise. After 2 hours and a further 3 hours, further portions of trifluoroacetic acid were added (2×2 mL). The reaction mixture was stirred at room temperature for 7 hours in total and evaporated. The residue was redissolved in a 1:1 mixture of methanol/dichloromethane and the acidic solution was quenched to pH 7-8 by addition of MP-carbonate resin. The reaction mixture was filtered and the solvent was removed to afford a brown oil (0.1 g, 91%).
δH (d-4-methanol, 250 MHz) 1.05-1.20 (1H, m), 1.25-1.45 (1H, m), 1.60-1.70 (1H, d), 1.75-1.85 (1H, d), 2.15-2.45 (3H, m), 2.60-2.70 (1H, d), 3.00 (2H, s), 3.05-3.15 (1H, d), 3.65 (2H, s), 4.20 (1H, d), 4.20-4.40 (4H, m), 4.65 (1H, d), 6.88 (1H, s), 7.11 (1H, t), 7.78 (1H, dd), 7.93 (1H, s), 8.11 (1H, s).
MS (+ve ion electrospray) m/z 468 (MH+).

This material (100 mg, 0.2 mmol) was treated with hydrochloric acid in methanol (1M, 0.4 mL), then evaporated to dryness and triturated with ether, affording the title compound as a brown solid (102 mg).

Example 10

6-({4-[(6,7-Dihydro[1,4]dioxino[2,3-c]pyridazin-3-ylmethyl)amino]-1-piperidinyl}methyl)-7-fluoro-5,6-dihydro-3H-pyrrolo[1,2,3-de]quinoxalin-3-one, Enantiomer E1 hydrochloride

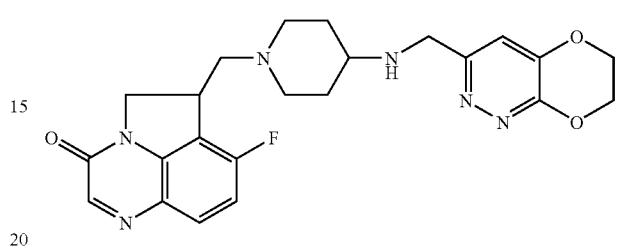

(a) 6-[(4-Amino-1-piperidinyl)methyl]-7-fluoro-5,6-dihydro-3H-pyrrolo[1,2,3-de]quinoxalin-3-one, Enantiomer E1

Racemic 6-[(4-amino-1-piperidinyl)methyl]-7-fluoro-5,6-dihydro-3H-pyrrolo[1,2,3-de]quinoxalin-3-one (7.9 g) was separated by chiral preparative HPLC using a Chiralpak AD® (20 u) column (101×250 mm), eluting with acetonitrile/methanol/isopropylamine (80:20:0.1, 400 ml/min) to give the E1 isomer (3.4 g), first eluting isomer, Rt 6.9 min,), ee>99%.

(b) Title Compound

A mixture of 6-[(4-amino-1-piperidinyl)methyl]-7-fluoro-5,6-dihydro-3H-pyrrolo[1,2,3-de]quinoxalin-3-one, Enantiomer E1 (2.28 g, 7.6 mmol) and 6,7-dihydro[1,4]dioxino[2,3-c]pyridazine-3-carbaldehyde (1.40 g, 8.5 mmol) in dry chloroform/methanol (1:1, 200 ml) was heated with 3 A molecular sieves under reflux overnight. After cooling, sodium triacetoxyborohydride (6.38 g, 30.4 mmol) was added and the mixture was stirred for ~8 h at room temperature. Further aldehyde (0.14 g) and triacetoxyborohydride (0.64 g) were added and the mixture was stirred overnight. The mixture was washed with aqueous sodium bicarbonate to basify and the aqueous phase was extracted four times with 10% methanol/dichloromethane. Combined organic fractions were dried and evaporated. Chromatography on silica (200 g), eluting with 0-20% methanol/dichloromethane gave the free base (2.27 g, 66%).
δH (CDCl$_3$, 250 MHz) 1.46 (2H, m), 1.92 (2H, m), 2.09 (1H, td, obscured by water peak), 2.22 (1H, td), 2.48 (1H, m), 2.56 (1H, m), 2.77 (1H, br d), 2.87 (1H, dd), 3.00 (1H, br d), 4.03 (2H, s+1H, m), 4.37 (2H, m), 4.49 (4H, m), 6.98 (1H, t), 7.07 (1H, s), 7.68 (1H, dd), 8.20 (1H, s)
LC/MS (+ve ion electrospray): m/z 453 [MH$^+$]

The free base in dichloromethane was treated with 0.5M hydrogen chloride in methanol (10.04 ml) and solvent was evaporated. The residue was dried to give the hydrochloride salt (2.37 g).

Example 11

6-({4-[(6,7-Dihydro[1,4]dioxino[2,3-c]pyridazin-3-ylmethyl)amino]-1-piperidinyl}methyl)-7-fluoro-5,6-dihydro-3H-pyrrolo[1,2,3-de]quinoxalin-3-one, Enantiomer E2 hydrochloride

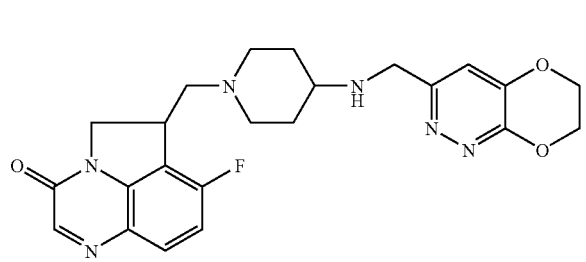

(a) 6-[(4-Amino-1-piperidinyl)methyl]-7-fluoro-5,6-dihydro-3H-pyrrolo[1,2,3-de]quinoxalin-3-one, Enantiomer E2

Racemic 6-[(4-amino-1-piperidinyl)methyl]-7-fluoro-5,6-dihydro-3H-pyrrolo[1,2,3-de]quinoxalin-3-one (7.9 g) was separated by chiral preparative HPLC using a Chiralpak AD® (20 u) column (101×250 mm), eluting with acetonitrile/methanol/isopropylamine (80:20:0.1, 400 ml/min) to give the E2 isomer (3.2 g), second eluting isomer, Rt 9.3 min,), ee>99%.

(b) Title Compound

A mixture of 6-[(4-amino-1-piperidinyl)methyl]-7-fluoro-5,6-dihydro-3H-pyrrolo[1,2,3-de]quinoxalin-3-one Enantiomer E2 (75 mg, 0.25 mmol) and 6,7-dihydro[1,4]dioxino[2,3-c]pyridazine-3-carbaldehyde (73 mg, 0.44 mmol) in dry chloroform/methanol (1:1, 7 ml) was heated with 3 A molecular sieves under reflux overnight. After cooling to room temperature, sodium triacetoxyborohydride (213 mg, 1.0 mmol) was added and the mixture was stirred for 8.5 h. The mixture was washed with aqueous sodium bicarbonate to basify and the aqueous phase was extracted three times with 10% methanol/dichloromethane. Combined organic fractions were dried and evaporated. Chromatography on silica (5 g), eluting with 0-20% methanol/dichloromethane gave the free base (30 mg 26.5%).

δH (CDCl$_3$, 250 MHz) 1.46 (2H, m), 1.92 (2H, m), 2.09 (1H, td), 2.22 (1H, td), 2.48 (1H, m), 2.56 (1H, m), 2.77 (1H, brd), 2.87 (1H, dd), 3.00 (1H, brd), 4.03 (2H, s+1H, m), 4.37 (2H, m), 4.49 (4H, m), 6.98 (1H, t), 7.07 (1H, s), 7.68 (1H, dd), 8.20 (1H, s)

LC/MS (+ve ion electrospray): m/z 453 [MH$^+$]

The free base in dichloromethane/chloroform was treated with 0.5M hydrogen chloride in methanol (0.13 ml) and solvent was evaporated. The residue was dried to give the hydrochloride salt (33 mg).

Example 12

6-({4-[(2,3-dihydro[1,4]dioxino[2,3-c]pyridin-7-ylmethyl)amino]-1-piperidinyl}methyl)-7-fluoro-6-hydroxy-5,6-dihydro-3H-pyrrolo[1,2,3-de]quinoxalin-3-one, Enantiomer E1 hydrochloride

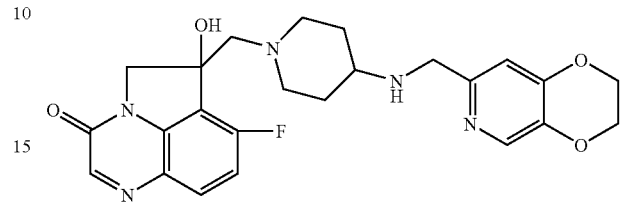

Racemic 6-({4-[(2,3-dihydro[1,4]dioxino[2,3-c]pyridin-7-ylmethyl)amino]-1-piperidinyl}methyl)-7-fluoro-6-hydroxy-5,6-dihydro-3H-pyrrolo[1,2,3-de]quinoxalin-3-one dihydrochloride (63 mg) (for a preparation, see Example 9(h)) was separated by chiral preparative HPLC using a Chiralpak AD-H® (5 u) column (21×250 mm), eluting with acetonitrile/methanol/isopropanol/isopropylamine (60:20:20:0.1, 20 ml/min) to give the E1 isomer, first eluting isomer, Rt 11.4 min, α$_D$ 22.9° C.+85° in methanol. Further elution with acetonitrile/isopropanol, isopropylamine (50:50: 0.1, 20 ml/min) gave the E2 isomer, Rt 21.7 min.

The E1 isomer was converted into the hydrochloride salt (24.2 mg) by treatment of a methanolic solution with 1 equivalent hydrochloric acid (6N) followed by stirring for 2 hours and evaporation of the solvent.

Example 12A 6-({4-[(2,3-dihydro[1,4]dioxino[2,3-c]pyridin-7-ylmethyl)amino]-1-piperidinyl}methyl)-7-fluoro-6-hydroxy-5,6-dihydro-3H-pyrrolo[1,2,3-de]quinoxalin-3-one, Enantiomer E1 dihydrochloride

(a) 1,1-Dimethylethyl {1-[(7-fluoro-6-hydroxy-3-oxo-5,6-dihydro-3H-pyrrolo[1,2,3-de]quinoxalin-6-yl)methyl]-4-piperidinyl}carbamate A mixture of (7-fluoro-6-hydroxy-3-oxo-5,6-dihydro-3H-pyrrolo[1,2,3-de]quinoxalin-6-yl)methyl 4-methylbenzenesulfonate (3.64 g, 9.3 mmol) (for a preparation, see Example 9(f)), 1,1-dimethylethyl 4-piperidinylcarbamate (2.0 g, 10.2 mmol) and sodium carbonate (2.9 g, 27.9 mmol) in ethanol (110 mL) and dimethylformamide (10 mL) was heated at 50° C. for 6 h. The mixture was evaporated to remove ethanol and the residue was partitioned between dichloromethane and half-saturated brine (200 mL each).

The aqueous phase was extracted with dichloromethane (200 mL) and the combined organic fractions were dried over sodium sulphate and evaporated. Chromatography on silica (2×100 g), eluting with 0-100% ethyl acetate/petroleum ether then 0-10% methanol/ethyl acetate gave a yellow foam (3.2 g, 82%).

MS (+ve ion electrospray) m/z 419 (MH+).

(b) 6-[(4-Amino-1-piperidinyl)methyl]-7-fluoro-6-hydroxy-5,6-dihydro-3H-pyrrolo[1,2,3-de]quinoxalin-3-one, Enantiomers E1 & E2

1,1-Dimethylethyl {1-[(7-fluoro-6-hydroxy-3-oxo-5,6-dihydro-3H-pyrrolo[1,2,3-de]quinoxalin-6-yl)methyl]-4-piperidinyl}carbamate (3.2 g, 7.7 mmol) was dissolved in dichloromethane (60 mL) and trifluoroacetic acid (30 mL). After 15 min. the mixture was evaporated and the residue was azeotroped with chloroform and triturated with ether. After drying under high vacuum, the resulting solid was dissolved in dichloromethane/methanol (1:1, 200 mL) and treated with MP-Carbonate resin (12 g, 2.6 mmol/g). After 0.5 h the resin was filtered off, washed with dichloromethane, methanol and dichloromethane again, and the filtrate evaporated to give racemic amine.

MS (+ve ion electrospray) m/z 319 (MH+).

2.5 g of racemic 6-[(4-amino-1-piperidinyl)methyl]-7-fluoro-6-hydroxy-5,6-dihydro-3H-pyrrolo[1,2,3-de]quinoxalin-3-one was resolved on Chiralpak AD® (20 u) (101× 250 mm; 20 u) using methanol (0.1% isopropylamine) at a flowrate of 400 ml/min and UV detection at 300 nm. After elution of the first enantiomer (Enantiomer E1) ([α]$_D$=+67° (c=0.3%, methanol)) the column was reverse flushed with isopropanol:acetonitrile:Isopropylamine-50:50:0.1 to elute the second enantiomer (Enantiomer E2). The recovery of Enantiomer E1 was 850 mg; >99% ee. The recovery of Enantiomer E2 was 630 mg; >99% ee.

(c) Title Compound

A solution of 6-[(4-amino-1-piperidinyl)methyl]-7-fluoro-6-hydroxy-5,6-dihydro-3H-pyrrolo[1,2,3-de]quinoxalin-3-one, Enantiomer E1 (300 mg, 0.942 mmol) and 2,3-dihydro[1,4]dioxino[2,3-c]pyridine-7-carboxaldehyde (for a synthesis see WO2004058144 Example 2(c) or WO03/087098 Example 19(d)) (125.0 mg, 0.757 mmol) in anhydrous dichloromethane (5 ml) and anhydrous methanol (1 ml) was stirred at room temperature, under argon, for 5 minutes and then treated with sodium triacetoxyborohydride (480.0 mg, 2.26 mmol) and stirred for 19 hours. The reaction mixture was treated with saturated aqueous NaHCO$_3$ solution (20 ml) and 19:1 dichloromethane:methanol (20 ml). The layers were separated and the aqueous layer was washed with 19:1 dichloromethane:methanol (2×20 ml). The organic extracts were combined, passed through a phase separator and evaporated to a dark orange gum. Purification on a 50 g silica column eluting with a 0 to 30% methanol in dichloromethane, 30 minute gradient gave the product, after evaporation, treatment with anhydrous diethyl ether and evaporation, as pale yellow foam (246.6 mg, 56%).

MS (+ve ion electrospray) m/z 468 (MH⁺).

δH (CDCl$_3$, 400 MHz) 1.46-1.62 (2H, m), 1.93-1.97 (2H, m), 2.35-2.41 (1H, m), 2.52-2.65 (2H, m), 2.81 (1H, d), 2.95 (2H, m), 3.35 (1H, d), 3.82 (2H, s), 4.27-4.45 (6H, m), 6.83 (1H, s), 6.99-7.04 (1H, m), 7.77-7.80 (1H, m), 8.11 (1H, s) and 8.22 (1H, s)

The free base was dissolved in dichloromethane (5 ml) and treated with 1M HCl in ether (5 ml). The resulting thick suspension was treated with anhydrous diethyl ether (20 ml), cooled, filtered, washed with diethyl ether and dried to give the product as a cream solid (286 mg).

Example 13

6-({4-[(2,3-dihydro[1,4]dioxino[2,3-c]pyridin-7-ylmethyl)amino]-1-piperidinyl}methyl)-7-fluoro-6-hydroxy-5,6-dihydro-3H-pyrrolo[1,2,3-de]quinoxalin-3-one, Enantiomer E2 hydrochloride

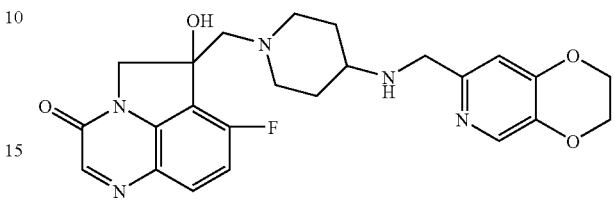

Racemic 6-({4-[(2,3-dihydro[1,4]dioxino[2,3-c]pyridin-7-ylmethyl)amino]-1-piperidinyl}methyl)-7-fluoro-6-hydroxy-5,6-dihydro-3H-pyrrolo[1,2,3-de]quinoxalin-3-one dihydrochloride (63 mg) was separated by chiral preparative HPLC using a Chiralpak AD-H® (5 u) column (21×250 mm), eluting with acetonitrile/methanol/isopropanol/isopropylamine (60:20:20:0.1, then 50:0:50:0.1, 20 ml/min) to give the E2 isomer, second eluting isomer, Rt 21.7 min, α$_D$ 22.9° C.-82° in methanol.

The E2 isomer was converted into the hydrochloride salt (21.5 mg) by treatment of a methanolic solution with 1 equivalent of hydrochloric acid (6N) followed by stirring for 2 hours and evaporation of the solvent.

Example 13A

6-({4-[(2,3-Dihydro[1,4]dioxino[2,3-c]pyridin-7-ylmethyl)amino]-1-piperidinyl}methyl)-7-fluoro-6-hydroxy-5,6-dihydro-3H-pyrrolo[1,2,3-de]quinoxalin-3-one, Enantiomer E2 dihydrochloride

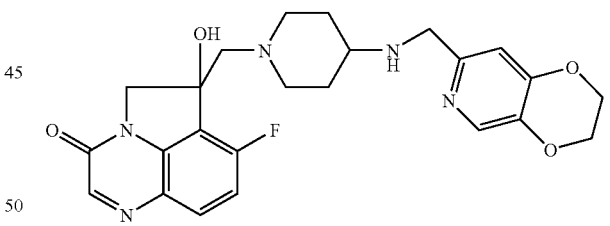

A solution of 6-[(4-amino-1-piperidinyl)methyl]-7-fluoro-6-hydroxy-5,6-dihydro-3H-pyrrolo[1,2,3-de]quinoxalin-3-one Enantiomer 2 (50 mg, 0.157 mmol) and 2,3-dihydro[1,4]dioxino[2,3-c]pyridine-7-carbaldehyde (for a synthesis see WO2004058144 Example 2(c) or WO03/087098 Example 19(d)) (20.8 mg, 0.126 mmol) in anhydrous dichloromethane (1 ml) and anhydrous methanol (0.2 ml) was stirred at room temperature, under argon, for 2 minutes and then treated with sodium triacetoxyborohydride (80 mg, 0.377 mmol) and stirred for 2 hours. The reaction mixture was treated with saturated aqueous NaHCO$_3$ solution (3 ml) and carefully shaken. The layers were separated and the aqueous layer was washed with 19:1 dichloromethane methanol (2×3 ml). The organic extracts were combined, passed through a phase separator and evaporated to a dark orange gum. Purification on a 10 g silica column eluted with a 0 to 30% methanol in dichloromethane, 30 minute gradient gave the product as an orange gum (51 mg, 68%).

MS (+ve ion electrospray) m/z 468 (MH+).

1H NMR (400 MHz) δ(CDCl3) 1.45-1.62 (2H, m), 1.93-1.97 (2H, m), 2.35-2.41 (1H, m), 2.52-2.65 (2H, m), 2.81 (1H, d), 2.95 (2H, m), 3.35 (1H, d), 3.80 (2H, s), 4.27-4.45 (6H, m), 6.82 (1H, s), 6.99-7.04 (1H, m), 7.77-7.80 (1H, m), 8.11 (1H, s) and 8.22 (1H, s)

The free base (51 mg) was dissolved in dichloromethane (2.5 ml) and treated with 1M HCl in ether (1 ml) and anhydrous diethyl ether (5 ml), cooled and centrifuged. The solvent was decanted off and the solid was dried to give the product as a cream solid (46.7 mg).

Example 14

6-({4-[(6,7-dihydro[1,4]oxathiino[2,3-c]pyridazin-3-ylmethyl)amino]-1-piperidinyl}methyl)-7-fluoro-5,6-dihydro-3H-pyrrolo[1,2,3-de]quinoxalin-3-one, Enantiomer E1 dihydrochloride

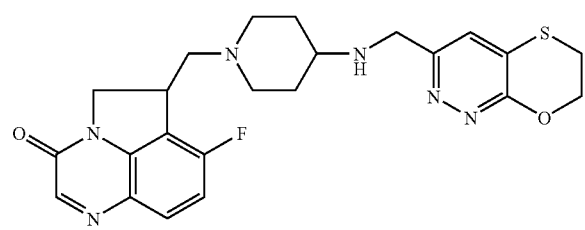

(a) 2-[(3,6-Chloro-4-pyridazinyl)thio]ethanol

A solution of 3,4,6-trichloropyridazine (25 g) in tetrahydrofuran (200 ml) and triethylamine (19 ml) was treated at 0° C. (ice bath cooling) with 2-mercaptoethanol (8.33 ml) over 5 minutes. After the addition was complete, the mixture was stirred at room temperature for 72 hours. The mixture was stirred with aqueous sodium bicarbonate solution and dichloromethane and the solid was collected, washed with water, ether and pentane and dried in vacuo, giving (22.9 g). The combined aqueous and organic fraction was evaporated to half volume giving further solid, which was washed and dried as above (5.0 g). The total yield of solid (27.9 g; 91%) contained some bromo-analogue (5-10%) by NMR.

(b) 3-Chloro-6,7-dihydro[1,4]oxathiino[2,3-c]pyridazine

A solution of 2-[(3,6-chloro-4-pyridazinyl)thio]ethanol (13 g) (previously dried at 50° C. in vacuo) in dry 1,4-dioxane (250 ml) was treated with lithium hydride (3 g) in portions and heated at 105-110° C. for 24 hours. The reaction mixture was cooled and quenched with iced-water. The solution was taken to pH 10-11 with 5M hydrochloric acid and evaporated. Water was added and the mixture was extracted 4× with dichloromethane, dried (sodium sulphate), evaporated, and chromatographed on silica gel, eluting with 0-100% ethyl acetate-hexane, to afford a white solid (1.61 g) (containing ca. 10% of the bromo species).

MS (+ve ion electrospray) m/z 189/91 (Cl MH+); 233/5 (Br MH+)

δH (CDCl3, 400 MHz) 3.23 (2H, m), 4.67 (2H, m), 7.26 (1H, s) (for major chloro-compound).

(c) 3-Ethenyl-6,7-dihydro[1,4]oxathiino[2,3-c]pyridazine

A solution of 3-chloro-6,7-dihydro[1,4]oxathiino[2,3-c]pyridazine (1.0 g) in dimethoxyethane (25 ml) was degassed under argon then tetrakis(triphenylphosphine)palladium (0) (135 mg), potassium carbonate (0.695 g), triethenylboroxin pyridine complex (0.8 g) and water (3.7 ml) were added. The mixture was heated overnight at 105° C. More triethenylboroxin pyridine complex (0.4 g) and tetrakis(triphenylphosphine)palladium (0) (30 mg) were added and heating was continued for 24 hours. The mixture was cooled, treated with aqueous sodium bicarbonate solution, extracted (4×) with dichloromethane, dried (sodium sulphate), evaporated and chromatographed on silica gel (70 g), eluting with 0-100% ethyl acetate-hexane, affording a solid (0.56 g) (87% pure by LC-MS).

MS (+ve ion electrospray) m/z 181 (MH+).

(d) 6,7-Dihydro[1,4]oxathiino[2,3-c]pyridazine-3-carbaldehyde

A solution of 3-ethenyl-6,7-dihydro[1,4]oxathiino[2,3-c]pyridazine (320 mg) in 1,4-dioxane/water (20 ml/5 ml) was treated with an aqueous solution of osmium tetroxide (4% w/v, 2 ml) and sodium periodate (1.08 g), initially stirred in an ice-bath, then allowed to warm to room temperature. After 2.5 hours the mixture was evaporated to dryness and dissolved in 1,4-dioxane and chloroform. Silica gel was added and the mixture was evaporated to dryness, added to a silica column (50 g) and chromatographed, eluting with 0-100% ethyl acetate in hexane, to afford a white solid (116 mg, 36%).

MS (+ve ion electrospray) m/z 183 (MH+).

(e) Title Compound

A solution of 6-[(4-amino-1-piperidinyl)methyl]-7-fluoro-5,6-dihydro-3H-pyrrolo[1,2,3-de]quinoxalin-3-one Enantiomer E1 (45 mg, 0.15 mmol) and 6,7-dihydro[1,4]oxathiino[2,3-c]pyridazine-3-carbaldehyde (30 mg, 0.165 mmol) in chloroform/methanol (1.25:1, 9 ml) was heated with 3 A molecular sieves at 70° C. overnight. After cooling, sodium triacetoxyborohydride (95 mg, 0.45 mmol) was added and the mixture was stirred for 5 h at room temperature. The mixture was washed with aqueous sodium bicarbonate and the aqueous phase was extracted three times with 10% methanol/dichloromethane. Combined organic fractions were dried and evaporated. Chromatography on silica, eluting with 0-20% methanol/dichloromethane gave the free base.

δH (CDCl3, 400 MHz) 1.42 (2H, m), 1.89 (2H, m), 2.09 (1H, td), 2.25 (1H, td), 2.49 (1H, m), 2.54 (1H, m), 2.77 (1H, br d), 2.87 (1H, dd), 3.00 (1H, br d), 3.02 (2H, m), 3.98 (2H, s), 4.02 (1H, m), 4.49 (2H, m), 4.65 (2H, m), 6.98 (1H, t), 7.35 (1H, s), 7.68 (1H, dd), 8.20 (1H, s)

LC/MS (+ve ion electrospray): m/z 469 [MH+]

The free base in methanol/chloroform was treated with 4M hydrogen chloride in 1,4-dioxane and solvent was evaporated. The residue was triturated with ether and dried to give the dihydrochloride salt (42 mg).

Example 15

6-({4-[(6,7-Dihydro-5H-pyrano[2,3-c]pyridazin-3-ylmethyl)amino]-1-piperidinyl}methyl)-7-fluoro-5,6-dihydro-3H-pyrrolo[1,2,3-de]quinoxalin-3-one, Enantiomer E1 dihydrochloride

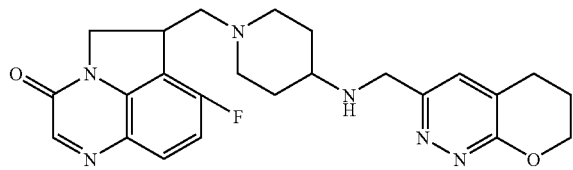

(a) 4-Bromo-2-{[4-(methyloxy)phenyl]methyl}-6-({[4-(methyloxy)phenyl]methyl}oxy)-3(2H)-pyridazinone and 5-bromo-2-{[4-(methyloxy)phenyl]methyl}-6-({[4-(methyloxy)phenyl]methyl}oxy)-3(2H)-pyridazinone A solution of 4-methoxybenzyl alcohol (6.2 ml, 50 mmol) in dry ether (120 ml) was treated dropwise with phosphorus tribromide (2.07 ml, 22 mmol). The mixture was heated under reflux for 1 hour, cooled, washed twice with water, dried and the solvent was evaporated. The 4-methoxybenzyl bromide thus produced was added to a mixture of 4-bromo-1,2-dihydro-3,6-pyridazinedione (for a synthesis, see Example 3(a) above) (4 g, 21 mmol) and potassium carbonate (8.28 g, 60 mmol) in dry DMF (60 ml) and stirred overnight at RT. The mixture was diluted with ethyl acetate, washed 3 times with water, dried over magnesium sulfate and evaporated to low volume. Some solid was filtered off and washed with ethyl acetate. The filtrate was evaporated to dryness and the residue chromatographed on silica, eluting with 20% ethyl acetate/hexane and then 100% ethyl acetate. This gave the less polar of the two desired products (3.233 g), the more polar of the two desired products (1.626 g) and a mixture of these (1.351 g). Total yield 6.30 g, 70%.

Less polar product MS (+ve ion electrospray) m/z 431 and 433 (MH$^+$, 15%), 121 (100%).

More polar product MS (+ve ion electrospray) m/z 431 and 433 (MH$^+$, 15%), 121 (100%).

(b) Butyl (2E)-3-[2-{[4-(methyloxy)phenyl]methyl}-6-({[4-(methyloxy)phenyl]methyl}oxy)-3-oxo-2,3-dihydro-4-pyridazinyl]-2-propenoate and butyl (2E)-3-[1-{[4-(methyloxy)phenyl]methyl}-3-({[4-(methyloxy)phenyl]methyl}oxy)-6-oxo-1,6-dihydro-4-pyridazinyl]-2-propenoate Argon was bubbled through a mixture of 4-bromo-2-{[4-(methyloxy)phenyl]methyl}-6-({[4-(methyloxy)phenyl]methyl}oxy)-3(2H)-pyridazinone and 5-bromo-2-{[4-(methyloxy)phenyl]methyl}-6-({[4-(methyloxy)phenyl]methyl}oxy)-3(2H)-pyridazinone (1.35 g, 3.14 mmol) in dry 1,4-dioxane (7.5 ml) for 20 minutes. The solution was then treated with bis(tri-t-butylphosphine)palladium(0) (32 mg, 0.0628 mmol), tris(dibenzylideneacetone)dipalladium(0) (29 mg, 0.0314 mmol), dicyclohexylmethylamine (0.74 ml, 3.45 mmol) and n-butyl acrylate (0.543 ml, 3.78 mmol), stirred under argon at RT 1 hour and at 95° C. overnight. The mixture was cooled and partitioned between ethyl acetate and water, separated, and the aqueous re-extracted with ethyl acetate. The combined organic solution was dried and evaporated and the residue was chromatographed, eluting with 15% ethyl acetate/hexane and then 35% ethyl acetate/hexane.

Less polar product (butyl (2E)-3-[2-{[4-(methyloxy)phenyl]methyl}-6-({[4-(methyloxy)phenyl]methyl}oxy)-3-oxo-2,3-dihydro-4-pyridazinyl]-2-propenoate) (838 mg, 55%).

MS (+ve ion electrospray) m/z 479 (MH$^+$, 70%), 121 (100%)

More polar product (butyl (2E)-3-[1-{[4-(methyloxy)phenyl]methyl}-3-({[4-(methyloxy)phenyl]methyl}oxy)-6-oxo-1,6-dihydro-4-pyridazinyl]-2-propenoate) (580 mg, 39%).

MS (+ve ion electrospray) m/z 479 (MH$^+$, 70%), 121 (100%)

(c) Butyl 3-(2-{[4-(methyloxy)phenyl]methyl}-3,6-dioxo-1,2,3,6-tetrahydro-4-pyridazinyl)propanoate A solution of butyl (2E)-3-[2-{[4-(methyloxy)phenyl]methyl}-6-({[4-(methyloxy)phenyl]methyl}oxy)-3-oxo-2,3-dihydro-4-pyridazinyl]-2-propenoate) (838 mg) in ethanol (15 ml)/1,4-dioxane (10 ml) was treated with 10% Pd/C (400 mg) and stirred under hydrogen at atmospheric pressure and RT for 2 hours. The catalyst was filtered off using kieselguhr and the filtrate was evaporated and redissolved in 1,4-dioxane and the solution evaporated to dryness to give the product as a colourless oil (0.56 g, 89%).

MS (+ve ion electrospray) m/z 361 (MH$^+$, 60%), 121 (100%)

(d) 5-(3-Hydroxypropyl)-1-{[4-(methyloxy)phenyl]methyl}-1,2-dihydro-3,6-pyridazinedione Butyl 3-(2-{[4-(methyloxy)phenyl]methyl}-3,6-dioxo-1,2,3,6-tetrahydro-4-pyridazinyl)propanoate (0.56 g, 1.56 mmol) was dissolved in dry THF (30 ml). The solution under argon was cooled to -30° C., treated dropwise with a 1M solution of lithium aluminium hydride in THF (1.8 ml, 1.8 mmol), allowed to warm gradually to 0° C. and stirred in an ice bath for 30 minutes. 2M Hydrochloric acid was added until pH 3 was obtained, and the mixture was partitioned between water and ethyl acetate. The aqueous was re-extracted with ethyl acetate and the combined organic solution dried and evaporated. Chromatography of the residue on silica, eluting with ethyl acetate, gave the product as a white solid (300 mg, 67%).

MS (+ve ion electrospray) m/z 291 (MH$^+$, 30%), 121 (100%)

(e) 4-(3-Hydroxypropyl)-1,2-dihydro-3,6-pyridazinedione 5-(3-Hydroxypropyl)-1-{[4-(methyloxy)phenyl]methyl}-1,2-dihydro-3,6-pyridazinedione (2.734 g) was treated with anisole (10 ml) and TFA (100 ml) and stirred at 40° C. overnight. The solution was cooled, evaporated to dryness and kept under high vacuum for 30 minutes. The residue was taken up in methanol (150 ml), refluxed for 12 hours, cooled and evaporated. The residue was kept for 1 hour under high vacuum, triturated under ether and the solid was filtered off. Drying under vacuum gave the product as a solid (1.48 g, 92%).

MS (+ve ion electrospray) m/z 171 (MH$^+$, 100%)

(f) 6,7-Dihydro-2H-pyrano[2,3-c]pyridazin-3(5H)-one

A suspension of 4-(3-hydroxypropyl)-1,2-dihydro-3,6-pyridazinedione (1.48 g, 8.7 mmol) in THF (105 ml) was held in an ultrasound bath for 5 minutes, then cooled under argon in an ice bath. Triphenylphosphine (3.67 g, 14 mmol) was added, followed by diisopropyl azodicarboxylate (2.76 ml, 14 mmol). After 30 minutes the solvent was evaporated and the residue kept under high vacuum overnight. Chromatography, eluting first with 2.5% methanol/dichloromethane until triphenylphosphine oxide was removed and then with 5% methanol/dichloromethane, gave the product as an off-white solid (1.049 g, 79%).

MS (+ve ion electrospray) m/z 153 (MH$^+$, 100%).

(g) Butyl 3-(1-{[4-(methyloxy)phenyl]methyl}-3,6-dioxo-1,2,3,6-tetrahydro-4-pyridazinyl)propanoate A solution of butyl (2E)-3-[1-{[4-(methyloxy)phenyl]methyl}-3-({[4-(methyloxy)phenyl]methyl}oxy)-6-oxo-1,6-dihydro-4-pyridazinyl]-2-propenoate (580 mg) in ethanol (15 ml)/1,4-dioxane (5 ml) was treated with 10% Pd/C (400 mg) and stirred under hydrogen at atmospheric pressure and RT for 2 hours. The catalyst was filtered off using kieselguhr and the filtrate was evaporated and redissolved in 1,4-dioxane and the solution evaporated to dryness to give the product (0.43 g, 98%).

MS (+ve ion electrospray) m/z 361 (MH$^+$, 50%), 121 (100%)

(h) 4-(3-Hydroxypropyl)-1-{[4-(methyloxy)phenyl]methyl}-1,2-dihydro-3,6-pyridazinedione Butyl 3-(1-{[4-(methyloxy)phenyl]methyl}-3,6-dioxo-1,2,3,6-tetrahydro-4-pyridazinyl)propanoate (0.43 g, 1.19 mmol) was dissolved in dry THF (20 ml). The solution under argon was cooled to −30° C., treated dropwise with a 1M solution of lithium aluminium hydride in THF (1.4 ml, 1.4 mmol), allowed to warm gradually to 0° C. and stirred in an ice bath for 30 minutes. 2M hydrochloric acid was added until the pH was 3 and the mixture was partitioned between water and ethyl acetate. The aqueous phase was re-extracted with ethyl acetate and the combined organic solution dried and evaporated. The resulting solid was triturated under ethyl acetate, filtered off, washed with ethyl acetate and dried under vacuum to give the product (241 mg, 70%).

MS (+ve ion electrospray) m/z 291 (MH$^+$, 10%), 121 (100%)

(i) 2-{[4-(Methyloxy)phenyl]methyl}-6,7-dihydro-2H-pyrano[2,3-c]pyridazin-3(5H)-one A suspension of 4-(3-hydroxypropyl)-1-{[4-(methyloxy)phenyl]methyl}-1,2-dihydro-3,6-pyridazinedione (2.624 g, 9.1 mmol) in THF (100 ml) was held in an ultrasound bath for 15 minutes. Triphenylphosphine (3.57 g, 13.6 mmol) was added under argon, the reaction mixture was then cooled to −10° C. and diisopropyl azodicarboxylate (2.68 ml, 13.6 mmol) was added, and the mixture was allowed to warm gradually to RT. After 1 hour the solvent was evaporated. Chromatography, eluting first with ethyl acetate to remove by-products and then with 10% ethanol/ethyl acetate, gave the product (2.55 g) contaminated with a little triphenylphosphine oxide.

MS (+ve ion electrospray) m/z 273 (MH$^+$, 50%), 121 (100%)

(j) 6,7-Dihydro-2H-pyrano[2,3-c]pyridazin-3(5H)-one

2-{[4-(Methyloxy)phenyl]methyl}-6,7-dihydro-2H-pyrano[2,3-c]pyridazin-3(5H)-one (2.75 g, 10.1 mmol) was treated with anisole (10 ml) and TFA (100 ml) and heated at 70° C. for 24 hours. The solution was cooled and evaporated and the residue taken up in 2.5% methanol/dichloromethane. This was applied to a column of silica, and then elution with this solvent mixture followed by 5% methanol/dichloromethane gave the product as an off white solid (1.36 g, 88%).

MS (+ve ion electrospray) m/z 153 (MH$^+$, 100%)

(k) 6,7-Dihydro-5H-pyrano[2,3-c]pyridazin-3-yl trifluoromethanesulfonate

A solution of 6,7-dihydro-2H-pyrano[2,3-c]pyridazin-3(5H)-one (152 mg, 1 mmol) in DMF (2.5 ml) under argon was ice-cooled, treated with sodium hydride (60 mg of a 60% dispersion in oil, 1.5 mmol) and stirred for 1 hour, allowing to warm to RT. N-Phenyl-bis(trifluoromethanesulfonimide) (505 mg, 1.4 mmol) was added and stirring continued for 2 hours. The mixture was diluted with ethyl acetate, washed with saturated aqueous sodium bicarbonate solution and water (twice), aqueous was reextracted with ethyl acetate and this was in turn washed with water. The combined organics were dried and evaporated. Chromatography, eluting with 40% ethyl acetate/hexane, gave the product as a white solid (228 mg, 80%).

MS (+ve ion electrospray) m/z 285 (MH$^+$, 100%)

(l) 3-Ethenyl-6,7-dihydro-5H-pyrano[2,3-c]pyridazine

Argon was bubbled for 15 minutes through a solution of 6,7-dihydro-5H-pyrano[2,3-c]pyridazin-3-yl trifluoromethanesulfonate (228 mg, 0.8 mmol) in 1,2-dimethoxyethane (6.5 ml). Tetrakis(triphenylphosphine)palladium(0) (50 mg, 0.0435 mmol) was added and the solution stirred for 20 minutes under argon. The mixture was then treated with potassium carbonate (111 mg, 0.8 mmol), water (1.9 ml) and triethenylboroxin pyridine complex (180 mg, 0.75 mmol). After stirring for 2 hours at 80° C., the mixture was cooled and partitioned between dichloromethane and saturated aqueous sodium bicarbonate solution. The layers were separated and the aqueous fraction was extracted twice with 20% methanol/dichloromethane. The combined organic solution was dried, evaporated and the residue chromatographed on silica, eluting with ethyl acetate to give the product as a white solid (100 mg, 77%).

MS (+ve ion electrospray) m/z 163 (MH$^+$, 100%).

(m) 6,7-Dihydro-5H-pyrano[2,3-c]pyridazine-3-carbaldehyde

A solution of 3-ethenyl-6,7-dihydro-5H-pyrano[2,3-c]pyridazine (100 mg, 0.617 mmol) in 1,4-dioxane (5.5 ml)/water (1.1 ml) was cooled in ice/water and treated with sodium periodate (306 mg, 1.43 mmol) and a 4% aqueous solution of osmium tetroxide (0.55 ml). The mixture was allowed to warm to RT after an hour, and after a total of 4.75 hours stirring, the solvent was evaporated. 1,4-Dioxane was added and evaporated, a few ml of dichloromethane were added and the mixture briefly held in an ultrasonic bath. The whole mixture was applied to a silica column and eluted with ethyl acetate to give the product (55 mg, 54%).

MS (+ve ion electrospray) m/z 165 (MH$^+$, 100%)

(n) Title Compound

A solution of 6-[(4-amino-1-piperidinyl)methyl]-7-fluoro-5,6-dihydro-3H-pyrrolo[1,2,3-de]quinoxalin-3-one Enantiomer E1 (30 mg, 0.1 mmol) and 6,7-dihydro-5H-pyrano[2,3-c]pyridazine-3-carbaldehyde (20.5 mg, 0.125 mmol) in chloroform/methanol (1:1, 2 ml) was heated with 3 A molecular sieves at 65° C. for 4 h. After cooling, sodium triacetoxyborohydride (42 mg, 0.2 mmol) was added and the mixture was stirred overnight at room temperature. The mixture was filtered through kieselguhr, washed through with 1:1 methanol/dichloromethane and evaporated. The residue was dissolved in 20% methanol/dichloromethane and washed with aqueous sodium bicarbonate. The aqueous phase was extracted twice with 20% methanol/dichloromethane. Combined organic fractions were dried and evaporated. Chromatography on silica, eluting with ammonia/methanol/dichloromethane (0.5:5:95) gave the free base (28 mg, 62%).

δH (CDCl$_3$, 400 MHz) 1.35-1.50 (2H, m), 1.85-2.00 (2H, m), 2.00-2.15 (3H, m), 2.15-2.30 (1H, m), 2.45-2.65 (2H, m), 2.76 (1H, d), 2.80-2.90 (3H, m), 3.00 (1H, d), 3.95-4.10 (3H, m), 4.35-4.55 (4H, m), 6.98 (1H, t), 7.29 (1H, s), 7.68 (1H, dd), 8.21 (1H, s).

MS (+ve ion electrospray) m/z 451 (MH$^+$, 100%)

The free base in chloroform was treated with 2 equivalents of 1M hydrogen chloride in ether and evaporated to give the dihydrochloride salt (33 mg).

Example 16

7-Fluoro-6-[(4-{[(1-oxo-1,2,3,4-tetrahydro-7-isoquinolinyl)methyl]amino}-1-piperidinyl)methyl]-5,6-dihydro-3H-pyrrolo[1,2,3-de]quinoxalin-3-one, Enantiomer E1 dihydrochloride

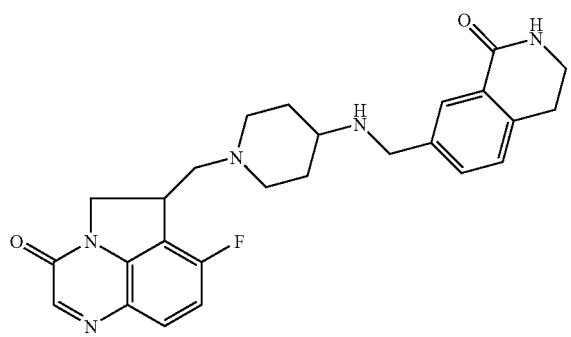

(a) 7-Bromo-3,4-dihydro-1(2H)-isoquinolinone

To a solution of 7-amino-3,4-dihydro-1(2H)-isoquinolinone, (for a synthesis see Girard, Yves; Atkinson, Joseph G.; Belanger, Patrice C.; Fuentes, Jose J.; Rokach, Joshua; Rooney, C. Stanley; Remy, David C.; Hunt, Cecilia A *J. Org. Chem.* (1983), 48(19), 3220) (0.773 g, 4.772 mmol) in acetonitrile (10 ml) at 0° C. was added 48% aqueous hydrobromic acid (10 ml, precooled to 0° C.). The mixture was stirred at 0° C. for 0.5 h before addition of a solution of sodium nitrite (0.379 g, 5.49 mmol) in water (2 ml) over 0.4 h. The reaction was then stirred at 0° C. for 0.5 h and then copper(I) bromide (0.822 g, 5.726 mmol) was added portionwise over 10 min. The reaction mixture was then warmed to room temperature, stirred at room temperature for 0.5 h and then at 70° C. for 1 h. The reaction mixture was then cooled to 0° C., water (60 ml) was added and the mixture stirred at 0° C. for 1 h before filtering and drying in vacuo. The residue was dissolved in 10% methanol/dichloromethane, dried with magnesium sulphate and evaporated to give the desired product (0.679 g, 63%).

MS (+ve ion electrospray) m/z 227 (MH+).

(b) 7-Ethenyl-3,4-dihydro-1(2H)-isoquinolinone

A solution of 7-bromo-3,4-dihydro-1(2H)-isoquinolinone (0.679 g, 3.004 mmol) and tetrakis(triphenylphosphine)palladium(0) (174 mg, 0.150 mmol) in 1,2-dimethoxyethane (30 ml) was stirred at room temperature for 0.5 h before addition of triethenylboroxin.pyridine complex (295 mg, 1.218 mmol), K$_2$CO$_3$ (415 mg, 3.004 mmol) and water (10 ml). The reaction was heated at reflux for 1.5 h before cooling to room temperature and addition of water (50 ml). The mixture was extracted with 10% methanol/dichloromethane (3×100 ml), the organic layers were dried with magnesium sulphate and evaporated. Chromatography on silica, eluting with 0-100% ethyl acetate/hexane, gave the product (456 mg, 88%).

MS (+ve ion electrospray) m/z 174 (MH+).

(c) 1-Oxo-1,2,3,4-tetrahydro-7-isoquinolinecarbaldehyde

To a solution of 7-ethenyl-3,4-dihydro-1(2H)-isoquinolinone (232 mg, 1.341 mmol) in 1,4-dioxane (15 ml) and water (3 ml) at 0° C. was added sodium periodate (660 mg, 3.08 mmol) and osmium tetroxide (1.5 ml of a 4% aqueous solution). The reaction mixture was warmed to room temperature and stirred for 0.5 h before evaporation of the reaction mixture. The residue was dissolved in 1,4-dioxane (50 ml) and evaporated again. The mixture was then dissolved in dichloromethane (100 ml), dried with magnesium sulphate and evaporated. Chromatography on silica, eluting with 0-100% ethyl acetate/hexane, gave the product (133 mg, 57%).

MS (+ve ion electrospray) m/z 176 (MH+).

(d) Title Compound

6-[(4-Amino-1-piperidinyl)methyl]-7-fluoro-5,6-dihydro-3H-pyrrolo[1,2,3-de]quinoxalin-3-one, Enantiomer E1 (74 mg, 0.246 mmol) and 1-oxo-1,2,3,4-tetrahydro-7-isoquinolinecarbaldehyde (43 mg, 0.246 mmol) were stirred in chloroform (2 mL) and methanol (0.2 mL) for 1 h at room temperature before addition of sodium triacetoxyborohydride (156 mg, 0.738 mmol). The mixture was then stirred for 1 h at room temperature and before addition of sat. aqueous sodium bicarbonate (10 ml). The mixture was extracted three times with 10% methanol/dichloromethane, the organic layers were dried with magnesium sulphate and evaporated. Chromatography on silica, eluting with 0-20% methanol/dichloromethane, gave the product (76 mg, 67%).

MS (+ve ion electrospray) m/z 462 (MH+).

δH (CDCl$_3$, 400 MHz) 1.45-1.60 (2H, m), 1.89-2.01 (2H, m), 2.03-2.12 (1H, m) 2.19-2.29 (1H, m), 2.45-2.52 (1H, m), 2.56-2.65 (1H, m), 2.78-2.81 (1H, m), 2.88 (1H, dd), 2.98 (2H, t), 3.01-3.09 (1H, m), 3.45-3.52 (2H, m), 3.88 (2H, s), 3.92-4.08 (1H, m), 4.48-4.55 (2H, m), 6.98 (1H, t), 7.15 (1H, brs), 7.20 (1H, d), 7.50 (1H, d), 7.67 (1H, dd), 8.02 (1H, s), 8.20 (1H, s)

The free base in methanol and chloroform was converted to the dihydrochloride salt by adding an equivalent of 4M hydrogen chloride in 1,4-dioxane, followed by evaporation to dryness (81 mg).

Example 17

6-({4-[(6,7-Dihydro[1,4]dioxino[2,3-c]pyridazin-3-ylmethyl)amino]-1-piperidinyl}methyl)-7-fluoro-6-hydroxy-5,6-dihydro-3H-pyrrolo[1,2,3-de]quinoxalin-3-one, Enantiomer E1 dihydrochloride

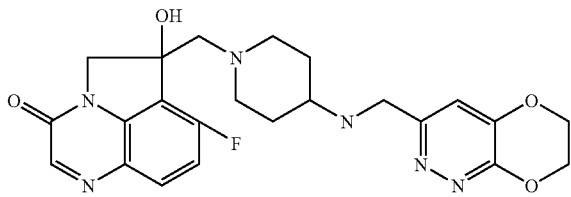

A solution of 6-[(4-amino-1-piperidinyl)methyl]-7-fluoro-6-hydroxy-5,6-dihydro-3H-pyrrolo[1,2,3-de]quinoxalin-3-one Enantiomer E1 (50 mg, 0.157 mmol) and 6,7-dihydro[1,4]dioxino[2,3-c]pyridazine-3-carbaldehyde (26 mg, 0.157 mmol) in anhydrous dichloromethane (1 mL) and methanol (0.2 mL) was shaken for 5 min., then sodium triacetoxyborohydride (80 mg, 0.38 mmol) was added and shaking continued for 18 h. More aldehyde (13 mg) and triacetoxyborohydride (40 mg) were added and shaking continued for 5 h. Aqueous sodium bicarbonate was added and the phases were separated. The aqueous phase was extracted twice with 5% methanol/dichloromethane and the organic fractions were dried and evaporated. Chromatography on silica, eluting with 0-30% methanol/dichloromethane gave the free base (37 mg, 50%)

δH (CDCl$_3$, 400 MHz) 1.50 (2H, m, part. obscured by water), 1.96 (2H, m), 2.38 (1H, t), 2.55 (1H, t), 2.60 (1H, m), 2.82 (1H, d), 2.96 (2H, m), 3.36 (1H, d), 4.02 (2H, s), 4.38 (2H, m), 4.41 (2H, m), 4.52 (2H, m), 7.03 (2H, m), 7.79 (1H, dd), 8.22 (1H, s).

MS (+ve ion electrospray) m/z 469 (MH+).

The free base in chloroform was treated with 1M HCl in ether (10 mL). The resulting suspension was treated with ether, cooled and centrifuged, and the solid was dried to give the dihydrochloride salt (39 mg).

Example 18

7-fluoro-6-[(4-{[(7-oxo-1,5,6,7-tetrahydropyrido[2,3-d]pyrimidin-2-yl)methyl]amino}-1-piperidinyl)methyl]-5,6-dihydro-3H-pyrrolo[1,2,3-de]quinoxalin-3-one, Enantiomer E1 hydrochloride

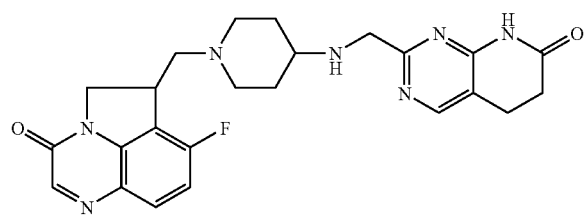

(a) 3-Ethyl 1,1-dimethyl 1,1,3-propanetricarboxylate

To a solution of dimethyl malonate (2.5 g, 18.9 mmol) in anhydrous THF (20 mL) was added NaH (0.038 g, 0.95 mmol, 60% in mineral oil). The reaction was stirred at ambient temperature for 15 minutes. In a separate flask, ethyl acrylate was dissolved in anhydrous THF (1 mL) and then added dropwise over 30 minutes to the dimethyl malonate solution. The reaction was stirred at ambient temperature for 16 h and then concentrated under vacuum. The residue was dissolved in EtOAc (ethyl acetate) and washed with saturated NH$_4$Cl solution and brine. The organic phase was dried over Na$_2$SO$_4$, filtered, and concentrated under vacuum. The crude residue was purified by column chromatography (silica gel) using an EtOAc/hexanes gradient to yield the desired compound as a colorless oil (1.68 g, 77%).

$^1$H NMR (400 MHz, CDCl$_3$) δ 1.24 (t, J=7.07 Hz, 3H) 2.20 (q, J=7.24 Hz, 2H) 2.37 (t, J=7.33 Hz, 2H) 3.47 (t, J=7.33 Hz, 1H) 3.70-3.75 (m, 6H) 4.12 (q, J=7.24 Hz, 2H).

(b) (2E)-3-Phenyl-2-propenimidamide

Cinnamonitrile (25.0 g, 194 mmol) was dissolved in EtOH (ethanol) (200 mL). The solution was cooled to 0° C. and HCl gas bubbled through the solution for 30 minutes. The solution was stirred at ambient temperature for 16 h and then concentrated under vacuum. The residue was dissolved in EtOH (100 mL), cooled to 0° C. and a solution of NH$_3$/MeOH (7M, 69 mL, 484 mmol) was added dropwise through an addition funnel. Once added, the solution was allowed to warm to ambient temperature and the resulting NH$_4$Cl was filtered off. The solution was concentrated under vacuum and the resulting white solid was used without further purification (26 g crude).

LCMS: m/z 147.4 (MH+).

(c) Ethyl 3-{4-hydroxy-6-oxo-2-[(E)-2-phenylethenyl]-1,6-dihydro-5-pyrimidinyl}propanoate 3-Ethyl 1,1-dimethyl 1,1,3-propanetricarboxylate (1.65 g, 7.11 mmol) and (2E)-3-phenyl-2-propenimidamide (1.04 g, 7.11 mmol) were combined in EtOH (36 mL). Triethylamine (1.98 mL, 14.2 mmol) was added and the solution was heated at reflux for 3 h with no change based on LCMS. The solution was cooled to room temperature and treated with NaOMe in MeOH (1.0 mL, 5.33 mmol, 25% wt solution) and the solution was refluxed for an additional 4 h. Another portion of NaOMe in MeOH (1.0 mL, 5.33 mmol, 25% wt solution) was added and the solution was refluxed for 16 h. After this time, a yellow precipitate had formed which was filtered off. The mother liquor was acidified to pH2 with 1N HCl, and the solution was concentrated under vacuum. The resulting material was combined with the yellow solid and used without further purification.

LCMS: m/z 315.2 (MH+).

(d) Ethyl 3-{4,6-dichloro-2-[(E)-2-phenylethenyl]-5-pyrimidinyl}propanoate

Crude ethyl 3-{4-hydroxy-6-oxo-2-[(E)-2-phenylethenyl]-1,6-dihydro-5-pyrimidinyl}propanoate was dissolved in POCl$_3$ (25 mL) and N,N-dimethylaniline (0.9 mL, 7.1 mmol) was slowly added to the solution. The reaction was then heated at reflux for 2 h. After cooling to ambient temperature, the resulting solution was carefully and slowly added to ice water to quench the excess POCl$_3$. The mixture was extracted with EtOAc (3×), dried over Na$_2$SO$_4$, filtered and concentrated under vacuum. The crude residue was then purified by column chromatography (silica gel) using an EtOAc/hexanes gradient to yield the desired compound as a yellow solid (0.48 g, 19% over 2 steps).

LCMS: m/z 351.4 (MH+).

(e) 4-Chloro-2-[(E)-2-phenylethenyl]-5,8-dihydropyrido[2,3-d]pyrimidin-7(6H)-one To a solution of ethyl 3-{4,6-dichloro-2-[(E)-2-phenylethenyl]-5-pyrimidinyl}propanoate (0.42 g, 1.19 mmol) in 1,4-dioxane (5 mL) was added conc. $NH_4OH$ (3.5 mL). The reaction was heated at 75° C. in a sealed tube for 16 h. The solution was concentrated under vacuum, diluted with water, and extracted with EtOAc. The organic layer was washed with brine, dried over $Na_2SO_4$, and concentrated under vacuum. The crude residue was then purified by column chromatography (silica gel) to yield the desired compound as a yellow solid (0.072 g, 21%).

LCMS: m/z 286.2 (MH+).

Also obtained was 3-{4-amino-6-chloro-2-[(E)-2-phenylethenyl]-5-pyrimidinyl}propanamide as a white solid (0.175 g).

LCMS: m/z 303.3 (MH+).

3-{4-Amino-6-chloro-2-[(E)-2-phenylethenyl]-5-pyrimidinyl}propanamide (0.175 g, 0.58 mmol) was dissolved in EtOH (15 mL) and HCl gas was bubbled through the solution until saturated. The solution was heated at reflux for 2 h, cooled to ambient temperature and concentrated under vacuum. The residue was dissolved in water and extracted with EtOAc (3×). The organic layers were combined, dried over $Na_2SO_4$, filtered and concentrated under vacuum to yield ethyl 3-{4-amino-6-chloro-2-[(E)-2-phenylethenyl]-5-pyrimidinyl}propanoate as a white solid. LCMS: m/z 332.2 (MH+). This product was then dissolved in DMF (5 mL), treated with $K_2CO_3$ (0.16 g, 1.16 mmol) and heated at 75° C. for 30 minutes. The solution was cooled, diluted with water and extracted with $Et_2O$ (3×). The organic layer was dried over $Na_2SO_4$, filtered, and concentrated under vacuum. The crude residue was then purified by column chromatography (silica gel) to yield an additional 0.11 g of the desired compound as an off-white solid.

LCMS: m/z 286.2 (MH+).

(f) 4-Chloro-7-oxo-5,6,7,8-tetrahydropyrido[2,3-d]pyrimidine-2-carbaldehyde

4-Chloro-2-[(E)-2-phenylethenyl]-5,8-dihydropyrido[2,3-d]pyrimidin-7(6H)-one (0.18 g, 0.64 mmol) was dissolved in a 2:1 solution of 1,4-dioxane/water (6 mL) and cooled to 0° C. $NaIO_4$ (0.314 g, 1.47 mmol) and catalytic $OsO_4$ (1 mL, 4% aq. solution) were added and the solution was then stirred at ambient temperature for 16 h. The reaction solution was concentrated under vacuum, diluted with water, and extracted with 10% MeOH/DCM (4×). The organic layers were combined, dried over $Na_2SO_4$, filtered and concentrated under vacuum. The crude residue was then purified by column chromatography (silica gel) using a DCM/DCM-MeOH—$NH_4OH$ (90:10:1) gradient to yield the desired compound as an off-white solid (0.05 g, 44%).

LCMS: m/z 212.0 (MH+).

(g) 2-[Bis(methyloxy)methyl]-4-chloro-5,8-dihydropyrido[2,3-d]pyrimidin-7(6H)-one To a solution of 4-chloro-7-oxo-5,6,7,8-tetrahydropyrido[2,3-d]pyrimidine-2-carbaldehyde (1.43 g, 6.78 mmol) in MeOH (50 mL) was added p-toluenesulfonic acid monohydrate (p-TsOH.$H_2O$) (0.13 g, 0.68 mmol). The solution was heated at reflux for 3 h and then cooled to ambient temperature. The solution was concentrated under vacuum to yield the desired product as a white solid which was used without further purification.

LCMS: m/z 257.9 (MH+).

(h) 2-[Bis(methyloxy)methyl]-5,8-dihydropyrido[2,3-d]pyrimidin-7(6H)-one

To crude 2-[bis(methyloxy)methyl]-4-chloro-5,8-dihydropyrido[2,3-d]pyrimidin-7(6H)-one (prepared from 1.43 g 4-chloro-7-oxo-5,6,7,8-tetrahydropyrido[2,3-d]pyrimidine-2-carbaldehyde) dissolved in MeOH (50 mL) was added 10% Pd/C (wet) (0.15 g). The solution was stirred under an atmosphere of $H_2$ (balloon) overnight. The Pd/C was filtered off and the solution concentrated under vacuum. The crude residue was purified by column chromatography (silica gel) using a DCM/DCM-MeOH—$NH_4OH$ (90:10:1) gradient to yield the desired product as a white solid (0.873 g, 58% over 2 steps).

LCMS: m/z 223.9 (MH+).

(i) 7-Oxo-5,6,7,8-tetrahydropyrido[2,3-d]pyrimidine-2-carbaldehyde

To a solution of 2-[bis(methyloxy)methyl]-5,8-dihydropyrido[2,3-d]pyrimidin-7(6H)-one (0.87 g, 3.91 mmol) in 1:1 $H_2O$/acetone (10 mL) was added p-TsOH.$H_2O$ (0.074 g, 0.39 mmol) and the reaction was heated at reflux for 2 days. The reaction was not complete, so additional p-TsOH.$H_2O$ (0.20 g) was added and the solution was refluxed for an additional 1 day. After the disappearance of starting material, the solution was concentrated under vacuum to yield the desired product as a white solid and the crude material was used directly in the next step (1.023 g).

LCMS: m/z 178.0 (MH+).

(j) Title Compound

To a solution of 6-[(4-amino-1-piperidinyl)methyl]-7-fluoro-5,6-dihydro-3H-pyrrolo[1,2,3-de]quinoxalin-3-one, Enantiomer E1 (0.045 g, 0.15 mmol) in 1:1 MeOH/DCM (20 mL), was added crude 7-oxo-1,5,6,7-tetrahydropyrido[2,3-d]pyrimidine-2-carbaldehyde (0.052 g, 0.29 mmol), $NaHCO_3$ (0.088 g, 1.05 mmol), and excess $Na_2SO_4$. The solution was stirred at ambient temperature for 16 h, followed by addition of $Na(OAc)_3BH$ (0.095 g, 0.45 mmol). The resulting solution was stirred for an additional 2 h. The solution was then concentrated onto silica gel under vacuum and the crude residue purified by column chromatography on silica gel (first DCM/10% MeOH/DCM, then DCM/90:10:1 DCM/MeOH/$NH_4OH$) to yield the free base of the desired product as a yellowish oily film (0.026 g, 37%).

LCMS: m/z 464.1 (MH+).

$^1$H NMR (400 MHz, $CDCl_3$) δ 1.52-1.64 (m, 2H) 1.99 (t, J=115.92 Hz, 2H) 2.07-2.17 (m, 1H) 2.22-2.32 (m, 1H) 2.47-2.56 (m, 1H) 2.66-2.77 (m, 3H) 2.82 (d, J=10.61 Hz, 1H) 2.89 (dd, J=12.51, 4.42 Hz, 1H) 2.98 (t, J=7.71 Hz, 2H) 3.06 (d, J=11.37 Hz, 1H) 4.00-4.10 (m, 3H) 4.44-4.55 (m, 2H) 6.98 (t, J=8.97 Hz, 1H) 7.69 (dd, J=8.84, 4.04 Hz, 1H) 8.20 (s, 1H) 8.40 (s, 1H).

The free base dissolved in DCM and treated with 1M hydrogen chloride in diethyl ether and evaporated to dryness to give the hydrochloride salt as an off white solid.

Example 19

6-({4-[(6,7-dihydro-5H-pyrano[2,3-d]pyrimidin-2-ylmethyl)amino]-1-piperidinyl}methyl)-7-fluoro-5,6-dihydro-3H-pyrrolo[1,2,3-de]quinoxalin-3-one, Enantiomer E1 dihydrochloride

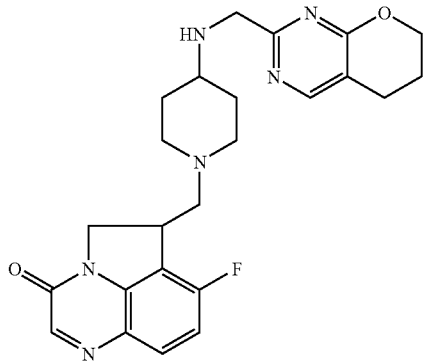

(a) 5-(3-Hydroxypropyl)-2-[(E)-2-phenylethenyl]-4(1H)-pyrimidinone

To δ-valerolactone (2.0 g; 20 mmol) in anhydrous diethyl ether (20 ml) was added ethyl formate (1.6 mL; 21 mmol) and sodium hydride (1.0 g of a 60% w:w dispersion in oil, 25 mmol). The reaction was allowed to stir at room temperature under nitrogen for 45 min. A solution of (2E)-3-phenyl-2-propenimidamide (2.92 g; 20 mmol) in EtOH (25 ml) was added, the mixture was then heated to 80° C. and stirred at this temperature for 4 hours. The reaction was cooled to room temperature, water was added (50 mL) and the mixture was extracted with EtOAc (2×200 mL). The combined organic extracts were dried with $Na_2SO_4$, the solvents were removed and the crude residues were purified by column chromatography on silica gel using a 0-10% MeOH/DCM gradient. Fractions containing product were concentrated to afford the desired compound (2.3 g, 45%).

MS (ES+) m/z 257 (MH+).

(b) 2-[(E)-2-Phenylethenyl]-6,7-dihydro-5H-pyrano[2,3-d]pyrimidine

To 5-(3-hydroxypropyl)-2-[(E)-2-phenylethenyl]-4(1H)-pyrimidinone (1.0 g; 4.0 mmol) in THF (20 ml) was added triphenyl phosphine (1.6 g; 6.0 mmol) and diethyl azodicarboxylate (1.0 g; 6.0 mmol). The reaction was allowed to stir at room temperature under nitrogen for 14 hours. The reaction was partitioned between water (20 ml) and EtOAc (100 ml), and the aqueous phase was further extracted with EtOAc (2×50 ml). The combined organic extracts were dried with $Na_2SO_4$, the solvents were removed and the crude residue was purified by column chromatography on silica gel using a 0-2.5% MeOH in DCM gradient to provide the desired compound (0.81 g; 84%).

MS (ES+) m/z 239 (MH+).

(c) 6,7-Dihydro-5H-pyrano[2,3-d]pyrimidine-2-carbaldehyde

2-[(E)-2-phenylethenyl]-6,7-dihydro-5H-pyrano[2,3-d]pyrimidine (0.5 g, 2.1 mmol) was dissolved in DCM (20 ml) and $O_3$ was bubbled through the reaction at −78° C. for 15 mins. Nitrogen was then bubbled through for 10 mins to remove the excess $O_3$ and the reaction was quenched with dimethyl sulfide (2.0 ml, 32.2 mmol). The reaction was allowed to warm to rt and was stirred for another 14 hours. All solvents were then removed to give the desired compound (0.28 g; 80%) which was used without further purification.

MS (ES+) m/z 165 (MH+).

(d) Title Compound

To a solution of 6-[(4-amino-1-piperidinyl)methyl]-7-fluoro-5,6-dihydro-3H-pyrrolo[1,2,3-de]quinoxalin-3-one, Enantiomer E1 (45 mg, 0.15 mmol) in chloroform (3 ml) and MeOH (0.3 ml) was added 6,7-dihydro-5H-pyrano[2,3-d]pyrimidine-2-carbaldehyde (25 mg; 0.15 mmol). The reaction was allowed to stir at room temperature for 16 hours followed by addition of $NaBH_4$ (7 mg; 0.18 mmol). The reaction was stirred for another 25 mins, the solvents were removed and the crude residue was purified by chromatography on silica gel using a 0-10% MeOH/DCM-94:5:1 DCM:MeOH:$NH_4OH$ gradient to provide the desired compound as the free base (22 mg; 33%).

MS (ES+) m/z 451 (MH+).

$^1$H NMR (400 MHz, $CDCl_3$) δ 1.51 (m, 2H), 1.89-2.12 (m, 4H), 2.04 (s, 3H), 2.24 (t, 1H), 2.50-2.74 (m, 2H), 2.80-2.91 (m, 3H), 3.33 (m, 1H) 3.85 (s, 2H), 4.45 (m, 1H), 4.85-4.93 (m, 3H), 7.10 (m, 1H), 7.73 (dd, 1H, J=8.8, 4.0 Hz), 8.14 (s, 1H), 8.34 (s, 1H).

The compound was converted to the di-HCl salt by dissolving the obtained free base in 10% MeOH/DCM and adding 1M HCl in diethyl ether. This was then evaporated to dryness.

Example 20

6-({4-[(6,7-dihydro[1,4]dioxino[2,3-d]pyrimidin-2-ylmethyl)amino]-1-piperidinyl}methyl)-7-fluoro-5,6-dihydro-3H-pyrrolo[1,2,3-de]quinoxalin-3-one, Enantiomer E1 dihydrochloride

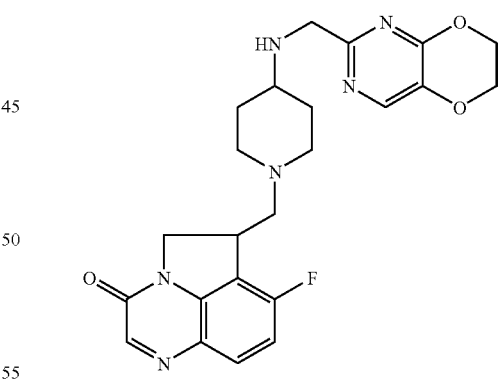

The title compound was prepared from 6-[(4-amino-1-piperidinyl)methyl]-7-fluoro-5,6-dihydro-3H-pyrrolo[1,2,3-de]quinoxalin-3-one, Enantiomer E1 and 6,7-dihydro-[1,4]dioxino[2,3-d]pyrimidin-2-carbaldehyde by a similar method to those described herein.

LC/MS: M+H at 453.0

$^1$H NMR (400 MHz, $CH_3OD$) δ ppm 2.32 (d, J=11.87, 2H) 2.53 (s, 2H) 3.66-3.77 (m, 3H) 3.86 (d, J=11.62 Hz, 1H) 4.09 (s, 1H) 4.36-4.42 (m, 2H) 4.42 (s, 2H) 4.58-4.67 (m, 5H) 7.20 (t, J=9.35 Hz, 1H) 7.84 (dd, J=8.84, 4.04 Hz, 1H) 8.19 (s, 1H) 8.31 (s, 1H).

Biological Activity

Antimicrobial Activity Assay:

Whole-cell antimicrobial activity was determined by broth microdilution using the Clinical and Laboratory Standards Institute (CLSI) recommended procedure, Document M7-A7, "Methods for Dilution Susceptibility Tests for Bacteria that Grow Aerobically". The compounds were tested in serial two-fold dilutions ranging from 0.016 to 16 mcg/mL.

Compounds were evaluated against a panel of Gram-positive organisms, including *Staphylococcus aureus, Streptococcus pneumoniae, Streptococcus pyogenes, Enterococcus faecalis* and *Enterococcus faecium*.

In addition, compounds were evaluated against a panel of Gram-negative organisms including *Haemophilus influenzae, Moraxella catarrhalis, Escherichia coli, Pseudomonas aeruginosa, Proteus mirabilis, Legionella pneumophila, Enterobacter cloacae, Enterobacter aerogenes, Klebsiella pneumoniae* and *Stenotrophomonas maltophilia*.

The *L. pneumophila* isolates were tested using a modified CLSI procedure for broth microdilution. For this assay, compounds were tested in serial doubling dilutions over a concentration range of 0.03 to 32 mcg/mL. An inoculum of each test isolate was prepared in buffered yeast broth and adjusted to a density equivalent to a 0.5 McFarland standard. After inoculation, the microtitre plates were incubated at 37° C. for 72 hours.

The minimum inhibitory concentration (MIC) was determined as the lowest concentration of compound that inhibited visible growth. A mirror reader was used to assist in determining the MIC endpoint.

Each of the listed Examples, as identified in the present application, were tested in at least one exemplified salt form. Unless otherwise noted, the listed Examples had a MIC≦2 µg/ml against a strain of at least one of the organisms listed above. For at least one strain of every organism listed above, at least one Example had a MIC≦2 µg/ml with the exception of strains of *Proteus mirabilis*, for which at least some Examples had a MIC≦16 µg/ml.

The invention claimed is:

1. A compound of formula (I) or a pharmaceutically acceptable salt thereof:

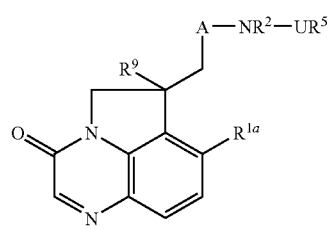

(I)

wherein:
R$^{1a}$ is selected from the group consisting of hydrogen; halo; cyano; (C$_{1-6}$)alkoxy, and (C$_{1-6}$)alkyl;
R$^2$ is hydrogen, or (C$_{1-4}$)alkyl;
A is a group (ia):

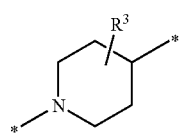

(ia)

in which: R$^3$ is hydrogen, halogen, C$_{1-6}$alkyl, or hydroxy;
U is CO or CH$_2$ and
R$^5$ is selected from the group consisting of:
3-oxo-3,4-dihydro-2H-pyrido[3,2-b][1,4]oxazin-6-yl;
2,3-dihydrofuro[2,3-c]pyridin-5-yl;
6,7-Dihydro[1,4]dioxino[2,3-c]pyridazin-3-yl;
6,7-dihydro[1,4]oxathiino[2,3-c]pyridazin-3-yl;
2,3-dihydro-[1,4]dioxino[2,3-c]pyridin-7-yl; and
[1,3]oxathiolo[5,4-c]pyridin-6-yl; and
R$^9$ is hydrogen or hydroxy.

2. A compound according to claim 1 wherein R$^{1a}$ is hydrogen, methoxy, methyl, chloro or fluoro.

3. A compound according to claim 2 wherein R$^2$ is hydrogen.

4. A compound according to claim 3 wherein R$^3$ is in the 3-position and is cis to the NR$^2$ group and R$^3$ is hydrogen or hydroxy.

5. A compound according to claim 4 wherein U is CH$_2$.

6. A compound according to claim 1 or a pharmaceutically acceptable salt thereof, which compound is selected from the group consisting of
6-({4-[(2,3-Dihydro[1,4]dioxino[2,3-c]pyridin-7-ylmethyl)amino]-1-piperidinyl}methyl)-7-fluoro-5,6-dihydro-3H-pyrrolo[1,2,3-de]quinoxalin-3-one or an enantiomer thereof;
6-({4-[(6,7-Dihydro[1,4]dioxino[2,3-c]pyridazin-3-ylmethyl)amino]-1-piperidinyl}methyl)-7-fluoro-5,6-dihydro-3H-pyrrolo[1,2,3-de]quinoxalin-3-one;
6-({4-[(2,3-Dihydrofuro[2,3-c]pyridin-5-ylmethyl) amino]-1-piperidinyl}methyl)-7-fluoro-5,6-dihydro-3H-pyrrolo[1,2,3-de]quinoxalin-3-one;
7-Fluoro-6-[(4-[[(3-oxo-3,4-dihydro-2H-pyrido[3,2-b][1,4]oxazin-6-yl)methyl]amino]-1-piperidinyl)methyl]-5,6-dihydro-3H-pyrrolo[1,2,3-de}quinoxalin-3-one;
6-({4-[(2,3-Dihydro[1,4]dioxino[2,3-c]pyridin-7-ylmethyl)amino]-1-piperidinyl}methyl)-7-fluoro-6-hydroxy-5,6-dihydro-3H-pyrrolo[1,2,3-de]quinoxalin-3-one;
6-({4-[(6,7-Dihydro[1,4]dioxino[2,3-c]pyridazin-3-ylmethyl)amino]-1-piperidinyl}methyl)-7-fluoro-5,6-dihydro-3H-pyrrolo[1,2,3-de]quinoxalin-3-one or an enantiomer thereof;
6-({4-[(2,3-dihydro[1,4]dioxino[2,3-c]pyridin-7-ylmethyl)amino]-1-piperidinyl}methyl)-7-fluoro-6-hydroxy-5,6-dihydro-3H-pyrrolo[1,2,3-de]quinoxalin-3-one or an enantiomer thereof;
6-({4-[(6,7-dihydro[1,4]oxathiino[2,3-c]pyridazin-3-ylmethyl)amino]-1-piperidinyl}methyl)-7-fluoro-5,6-dihydro-3H-pyrrolo[1,2,3-de]quinoxalin-3-one or an enantiomer thereof; and
6-({4-[(6,7-Dihydro[1,4]dioxino[2,3-c]pyridazin-3-ylmethyl)amino]-1-piperidinyl}methyl)-7-fluoro-6-hydroxy-5,6-dihydro-3H-pyrrolo[1,2,3-de]quinoxalin-3-one or an enantiomer thereof.

7. An enantiomer of 6-({4-[(2,3-dihydro[1,4]dioxino[2,3-c]pyridin-7-ylmethyl)amino]-1-piperidinyl}methyl)-7-fluoro-6-hydroxy-5,6-dihydro-3H-pyrrolo[1,2,3-de]quinoxalin-3-one hydrochloride.

8. A pharmaceutical composition comprising a compound according to claim 1 and a pharmaceutically acceptable carrier.

* * * * *